United States Patent [19]

Fujiwara et al.

[11] Patent Number: 5,026,832
[45] Date of Patent: Jun. 25, 1991

[54] 9-DIHYDRO-9-O-ALKYLDESMYCOSIN DERIVATIVES

[75] Inventors: Tatsuro Fujiwara; Yuji Kogami, both of Shizuoka; Asako Watanabe, Mishima, all of Japan

[73] Assignee: Toyo Jozo Co., Ltd., Shizuoka, Japan

[21] Appl. No.: 450,398

[22] Filed: Dec. 14, 1989

[30] Foreign Application Priority Data

Dec. 26, 1988 [JP] Japan .................................. 63-328327
Aug. 24, 1989 [JP] Japan .................................. 1-218327
Nov. 1, 1989 [JP] Japan .................................. 1-285228

[51] Int. Cl.$^5$ ...................... A61K 31/70; C07H 17/08
[52] U.S. Cl. ......................................... 536/7.1; 514/30
[58] Field of Search ............................ 536/7.1; 514/30

[56] References Cited

PUBLICATIONS

J. Med. Chem., 31, 1988, pp. 1631-1641, H. A. Kirst, et al., "Synthesis and Evaluation of Tylosin-Related Macrolides Modified at the Aldehyde Function: A New Series of Orally Effective Antibiotics".

Primary Examiner—Elli Peselev
Attorney, Agent, or Firm—Oblon, Spivak, McClelland, Maier & Neustadt

[57] ABSTRACT

9-Dihydro-9-O-alkyldesmycosin derivatives and their salts are disclosed. The 9-dihydro-9-O-alkyldesmycosin derivatives are represented by the following formula (I),

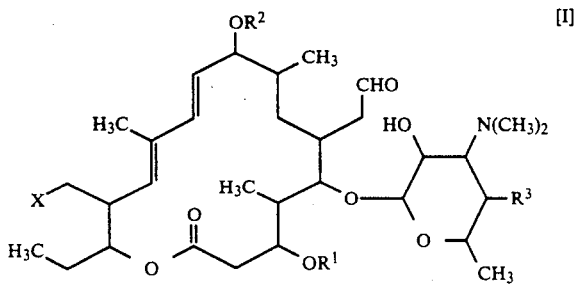

—wherein X represents an —O— mycinose or a di-lower alkylamino group, $R^1$ represents a hydrogen atom or a lower alkanoyl group, $R^2$ represents a lower alkyl group, a cycloalkyl-lower group, or phenyl-lower alkyl group which may have a substituent, and $R^3$ represents a hydrogen atom or a hydroxyl group. The compounds and the salts are useful as an antimicrobial agent. Unlike known desmycosin derivatives, the compounds give a high blood concentration by oral administration.

3 Claims, No Drawings

9-DIHYDRO-9-O-ALKYLDESMYCOSIN DERIVATIVES

BACKGROUND OF THE INVENTION

1. Field of the Invention

The present invention relates to 9-dihydro-9-O-alkyldesmycosin derivatives and salts thereof which are useful as an antimicrobial agent.

2. Description of the Background

Desmycosins (4'-demycarosyltylosins) do not produce a sufficiently high blood concentration by oral administration, and are thus incapable of providing a satisfactory infection curing effect. Various desmycosin derivatives have been prepared in an effort to find compounds which do not have this problem. For example, a desmycosin derivative having an improved bioavalability such as an improved blood concentration was prepared by modifying the 20-position aldehyde group of desmycosin [J. Med. Chem., 31, 1631–1641 (1988)]. There have been no published reports, however, dealing with modification of groups other than the aldehyde group in order to improve the in vivo efficiency of desmycosin. There is thus a strong desire for the development of a novel desmycosin derivative which can exhibit a satisfactory infection curing effect by oral administration.

In view of this situation, the present inventors have undertaken extensive studies concerning desmycosin derivatives. As a result the inventors found that 9-dihydro-9-O-alkyldesmycosin derivatives having a satisfactory infection curing effect by oral administration can be prepared by modifying the oxygen functional group bonding to position 9 of desmycosin. This finding has led to the completion of the present invention.

SUMMARY OF THE INVENTION

Accordingly, an object of the present invention is to provide 9-dihydro-9-O-alkyldesmycosin derivative represented by the following formula (I),

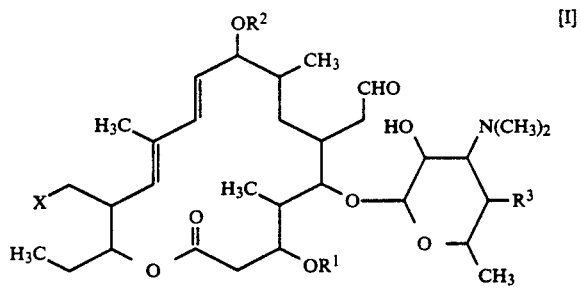

wherein X represents an —O— mycinose or a di-lower alkylamino group, $R^1$ represents a hydrogen atom or a lower alkanoyl group, $R^2$ represents a lower alkyl group, a cycloalkyl-lower alkyl group, or phenyl-lower alkyl group which may have a substituent, and $R^3$ represents a hydrogen atom or a hydroxyl group; or a salt thereof.

Other objects, features and advantages of the invention will hereinafter become more readily apparent from the following description.

DETAILED DESCRIPTION OF THE INVENTION AND PREFERRED EMBODIMENTS

In formula (I), a preferable lower alkanoyl group represented by $R^1$ is an alkanoyl group having 2-6 carbon atoms. Alkanoyl group having 2-4 carbon atoms is particularly preferable. Specific examples are acetyl, propionyl, butylyl, and the like. Among lower alkyl groups represented by $R^2$, those having 1-6 carbon atoms, especially 1-4 carbon atoms are preferable. Specific examples include methyl, ethyl, n-propyl, isopropyl, n-butyl, isobutyl, and the like. Preferable cycloalkyls in cycloalkyl-lower alkyl groups are those having 3-6 carbon atoms. Specific examples of cycloalkyl-lower alkyl groups are cyclopropylmethyl, cyclobutylmethyl, cyclopentylmethyl, cyclohexylmethyl, and the like. Given as examples of phenyl-lower alkyl groups are phenylmethyl, phenylethyl, phenylpropyl, and the like. The phenyl moiety may have a substituent such as a halogen atom, a lower alkyl group having 1-4 carbon atoms, a lower alkoxy group having 1-4 carbon atoms, or the like. As di-lower alkylamino groups represented by X, alkylamino groups having 1-6 carbon atoms are preferable. Specific examples are dimethylamino, diethylamino, dipropylamino, dibutylamino, and the like.

Especially preferable compounds (I) of the present invention are:
9-dihydro-9-O-methyldesmycosin, 9-dihydro-9-O-methyl-4'-deoxydesmycosin, 9-dihydro-9-O-ethyldesmycosin,
9-dihydro-9-O-ethyl-4'-deoxydesmycosin, 9-dihydro-9-O-propyldesmycosin, 9-dihydro-9-O-butyldesmycosin,
9-dihydro-9-O-isobutyldesmycosin, 9-dihydro-9-O-methyl-3-O-acetyldesmycosin, 9-dihydro-9-O-methyl-3-O-propionyldesmycosin, 9-dihydro-9-O-methyl-3-O-acetyl-4'-deoxydesmycosin, 9-dihydro-9-O-methyl-3-O-propionyl-4'-deoxydesmycosin, 9-dihydro-9-O-ethyl-3-O-acetyldesmycosin,
9-dihydro-9-O-ethyl-3-O-propionyldesmycosin, 9-dihydro-9-O-propyl-3-O-acetyldesmycosin, 9-dihydro-9-O-propyl-3-O-propionyldesmyco, 9-dihydro-9-O-butyl-3-O-acetyldesmycosin, 9-dihydro-9-O-butyl-3-O-propionyldesmycosin, 9-dihydro-9-O-isobutyl-3-O-acetyldesmycosin, 9-dihydro-9-O-isobutyl-3-O-propionyldesmycosin, 9-dihydro-9-O-cyclopropylmethyldesmycosin, 9-dihydro-9-O-cyclopropylmethyldesmycosin,
9-dihydro-9-O-cyclobutylmethyldesmycosin, 9-dihydro-9-O-cyclopentylmethyldesmycosin, 9-dihydro-9-O-cyclohexylmethyldesmycosin, 9-dihydro-9-O-cyclopropylmethyl-3-O-acetyldesmycosin, 9-dihydro-9-O-cyclopropylmethyl-3-O-propionyldesmycosin, 9-dihydro-9-O-cyclobutylmethyl-3-O-acetyldesmycosin, 9-dihydro-9-O-cyclobutylmethyl-3-O-propionyldesmycosin, 9-dihydro-9-O-cyclopentylmethyl-3-O-acetyldesmycosin, 9-dihydro-9-O-cyclopentylmethyl-3-O-propionyldesmycosin, 9-dihydro-9-O-cyclohexylmethyl-3-O-acetyldesmycosin, 9-dihydro-9-O-cyclohexylmethyl-3-O-propionyldesmycosin, 9-dihydro-9-O-cyclohexylmethyl-4'-deoxydesmycosin, 9-dihydro-9-O-benzyldesmycosin,
9-dihydro-9-O-benzyl-3-O-acetyldesmycosin, 9-dihydro-9-O-benzyl-3-O-propionyldesmycosin, 9-dihydro-9-O-benzyl-4'-deoxydesmycosin, or 9-dihydro-9-O-(2-phenylethyl)desmycosin.

A salt of Compound (I) of the present invention can be any pharmaceutically acceptable salt. It may be, for example, a salt of an inorganic acid such as chloride, sulfate, phosphate, or the like, or a salt of an organic acid such as acetate, propionate, citrate, succinate, malate, aspartate, glutamate, or the like.

In this specification, the nomenclature of compounds of formula (I) and their intermediates, especially the nomenclature of the bonding state of the atom or atomic groups bonding to the position 9 carbon atom, followed the description of "9-dihydroerythromysin" in page 92, Macrolid Antibiotics Chemistry, Biology and Practice, by Satoshi OMURA [(Academic Press Inc. (1984)].

Compound (I) of the present invention can be prepared, for example, by the following Processes (1)–(3).

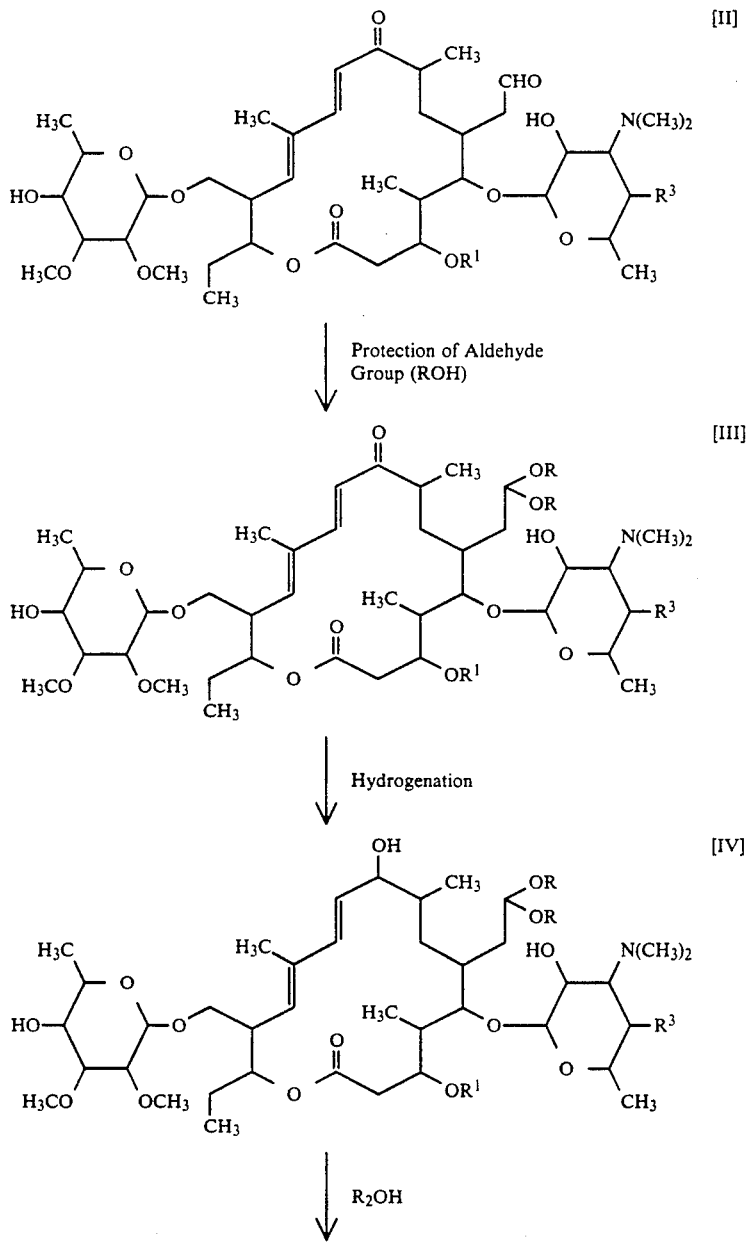

Process (1)

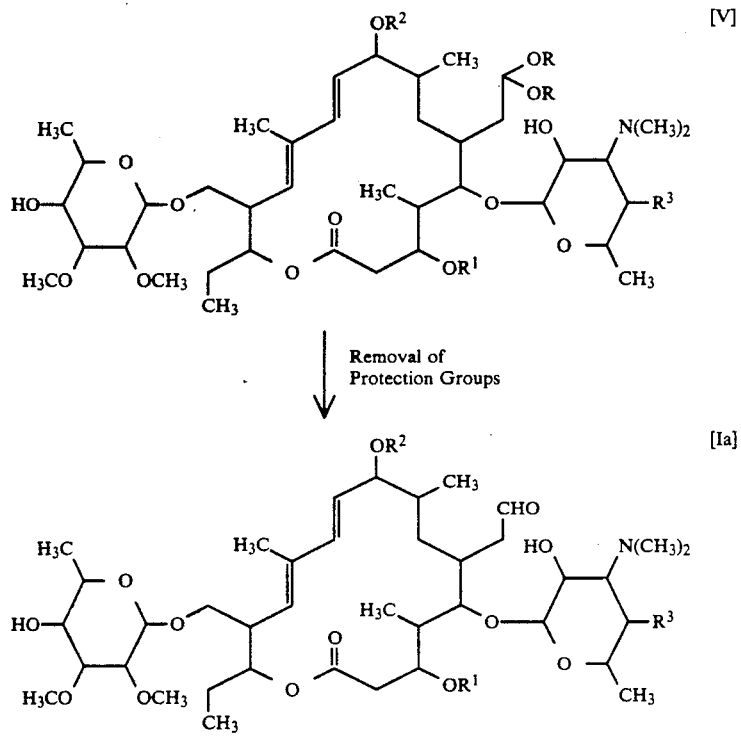

wherein $R^1$, $R^2$, and $R^3$ have the same meanings as defined above, and Rs independently represent a lower alkyl group or the two Rs in combination form a lower alkylene group.

According to the above reaction scheme, Compound (III) is prepared by protecting the aldehyde group of a desmycosin derivative (II). Compound (III) is hydrogenated by an alkaline-metal borohydride and converted into Compound (IV), which is reacted with an alcohol to produce Compound (V). An aldehyde protective group is removed from this Compound (V) to give Compound (Ia) of the present invention.

The raw material may be any known desmycosin derivative having the formula (II). Such a compound can be prepared according to the methods described, for example, in The Journal of Antibiotics, 34 (10), 1381-1384 (1981) or in Japanese Patent Laid-open No. 154197/1982.

Protection of the aldehyde group of Compound (II) can be carried out according to a known method. A preferable example of such a method is reacting Compound (II) with a lower alcohol (e.g. methanol, ethanol, propanol, etc.) or a lower glycol (e.g. ethylene glycol, propylene glycol, etc.) in the presence of an acid catalyst such as dichloroacetic acid, difluoroacetic acid, trifluoroacetic acid, p-toluenesulfonic acid, or the like. The reaction is carried out at a temperature of 10-30° C. for 5-16 hours.

Hydrogenation of Compound (III) is carried out using a 3-4 equivalent of an alkaline-metal borohydride such as sodium borohydride, preferably in a solvent such as methanol, at a temperature of 0° C to room temperature for 0.5-2 hours.

The reaction of Compound (IV) and an alcohol ($R^2$—OH) is preferably carried out using one of the above-mentioned acid catalysts at a temperature of 10°-30° C. for 16 hours to 7 days. Examples of a preferable alcohol ($R^2$—OH) used here is a linear lower alcohol such as methanol, ethanol, n-propanol, n-butanol, or the like.

Removal of the aldehyde protective group of Compound (V) is carried out according to a conventional method, for example, by reacting trifluoroacetic acid or the like with Compound (V) in a solvent such as an acetonitrile-water mixture at a temperature of 0° C. to room temperature for 30 minutes to 1 hour.

Process (2)
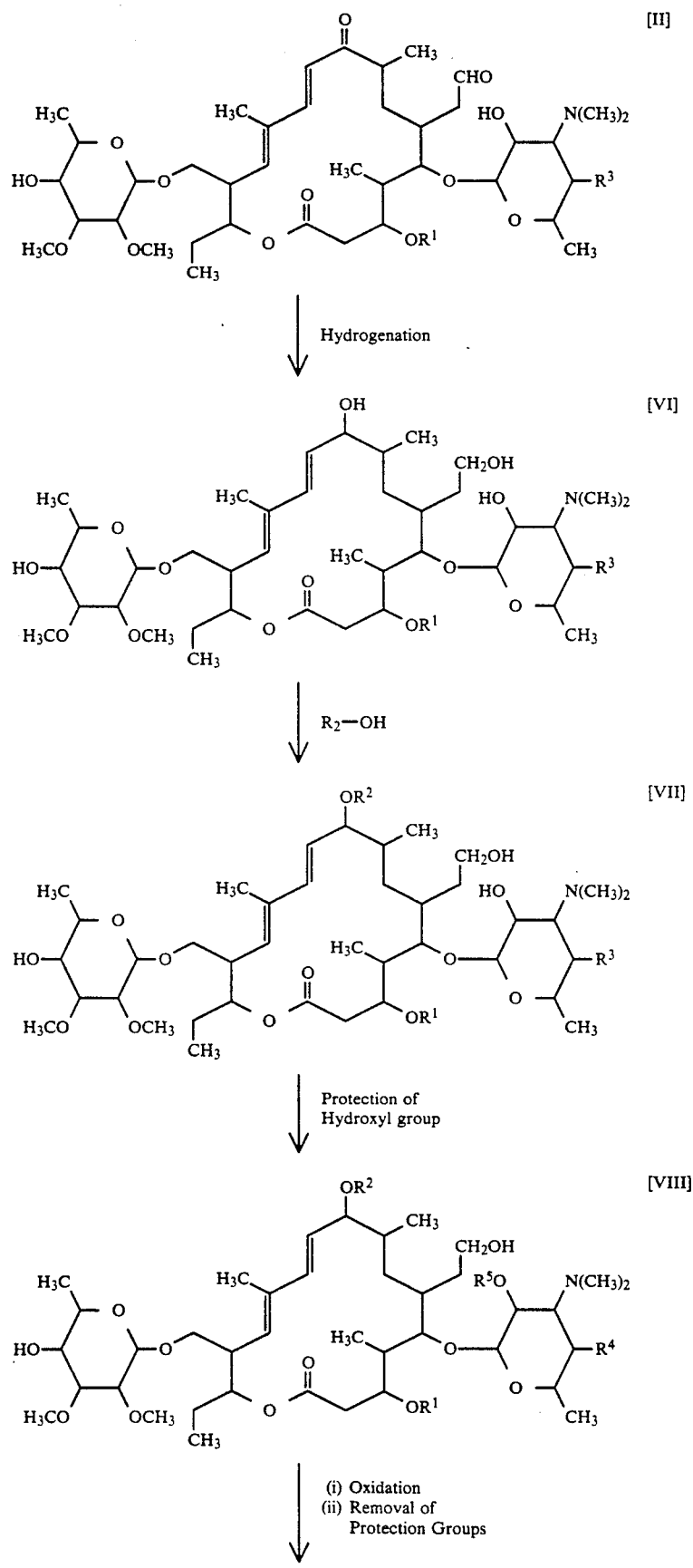

Process (2)

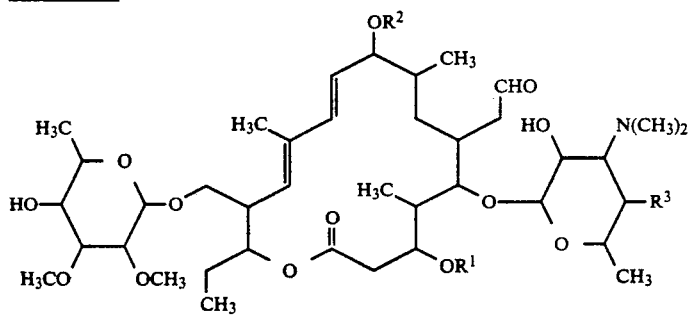

wherein R¹, R², and R³ have the same meanings as defined above and R⁴ represents a hydrogen atom or a group —OR⁵, wherein R⁵ is a hydroxyl protective group.

According to the above reaction scheme, a desmycosin derivative (II) is hydrogenated into Compound (VI) is reacted with an alcohol (R²—OH) to produce Compound (VII). The hydroxyl group at position 2' or the hydroxyl groups at positions 2' and 4' of Compound (VII) is protected to produce Compound (VIII), which is oxidized, followed by removal of the hydroxyl protective group at position 2' or at positions 2' and 4' to give Compound (Ib) of the present invention.

Desmycosin derivatives (II) can be prepared in the same manner as in Process (1).

Hydrogenation of Compound (II) is carried out using a 2-4 equivalent of an alkaline-metal borohydride such as sodium borohydride, preferably in a lower alcohol such as methanol, ethanol, propanol, or the like, at a temperature of 0° C. to room temperature for 0.5-2 hours.

The reaction of Compound (VI) and an alcohol (R²—OH) is preferably carried out using an acid catalyst such as dichloroacetic acid, difluoroacetic acid, trifluoroacetic acid, p-toluenesulfonic acid, or the like at a temperature of 10°-80° C. for 1-24 hours. Given as examples of alcohols (R²—OH) used here are methanol, ethanol, n-propanol, isopropanol, n-butanol, isobutanol, cyclopropylmethanol, cyclobutylmethanol, cyclopentylmethanol, cyclohexylmethanol, benzyl alcohol, phenylethanol, phenylpropanol, and the like.

Various acyl groups can be used for protecting the hydroxyl group at position 2' or the hydroxyl groups at positions 2'- and 4' of Compound (VII). Preferable examples of acyl groups are lower alkanoyl groups such as acetyl, propionyl, etc., and halogenated acetyl groups such as chloroacetyl, dichloroacetyl, trichloroacetyl, trifluoroacetyl, etc. An especially preferable group is acetyl.

Protection of the hydroxyl groups of Compound (VII) can be carried out according to a known method, for example, by acting an acylation agent such as an acid anhydride in an inert solvent such as methylene chloride at a temperature of 0° C. to room temperature for 30 minutes to 1 hour.

Oxidation of Compound (VIII) is preferably carried out using an oxidant such as pyridine sulfurtrioxide, chromium oxide, dicyclohexylcarbodiimide-trifluoroacetic acid-pyridinedimethylsulfurtrioxide, or the like in an amount of a 1-3 equivalent of Compound (VIII) in a solvent such as methylene chloride or the like at a temperature of 0° C. to room temperature for 0.5—2 hours.

Removal of the hydroxyl protective group is carried out according to a conventional method, for example, by heating in a lower alcohol which may contain water. A lower alcohol such as methanol, ethanol, or the like can be used. Methanol is an especially preferable lower alcohol for removing the acetyl group.

Process (3)

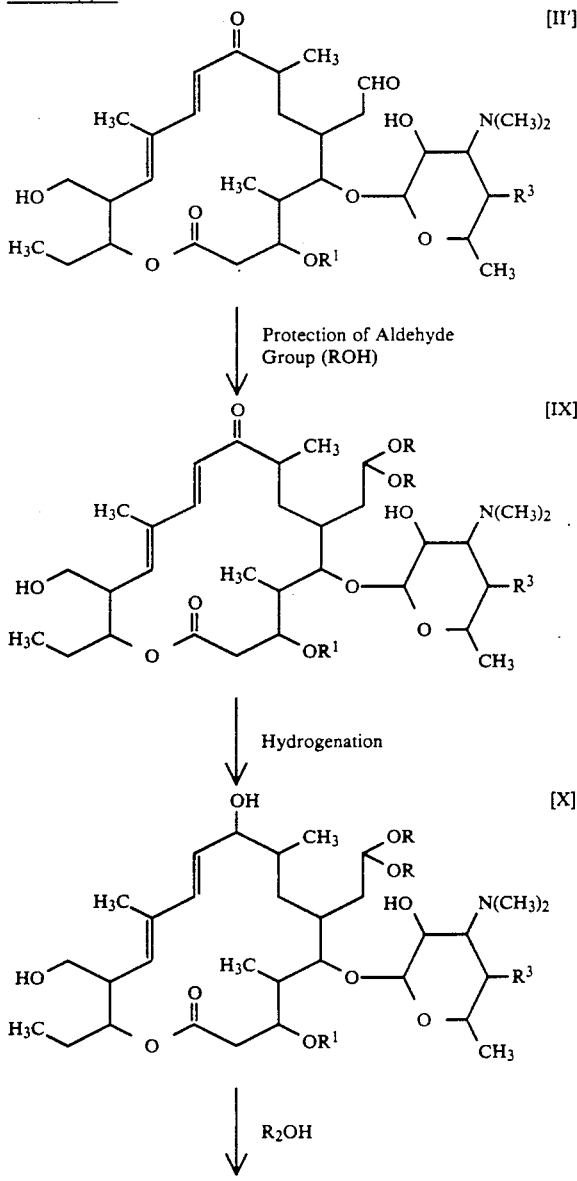

Process (3)
-continued

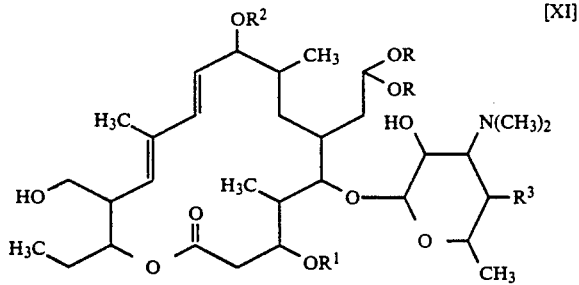

(i) Protection of hydroxyl group
(ii) p-Nitrobenzenesulfonyl halide

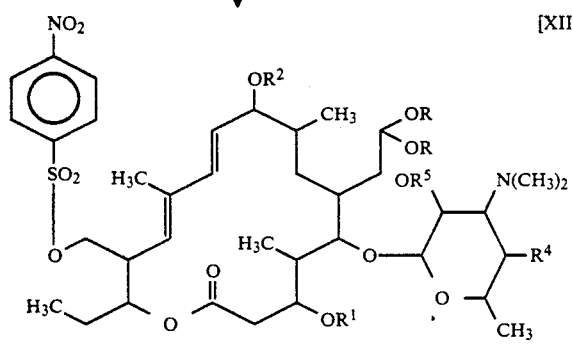

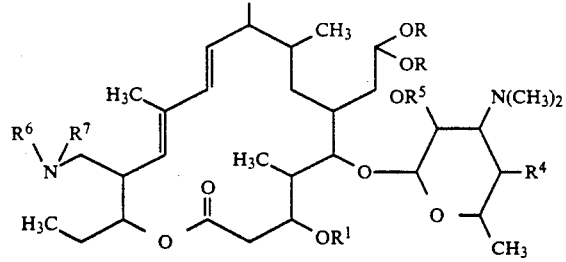

Removal of Protection Groups

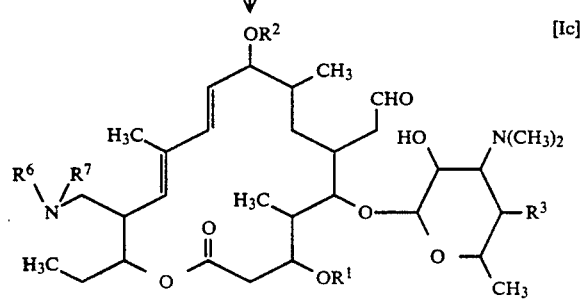

wherein $R^1$, $R^2$, $R^3$, $R^4$, $R^5$, and R have the same meanings as previously defined, and $R^6$ and $R^7$ represent lower alkyl groups.

In the same manner as Process (1), the aldehyde protection, hydrogenation, and reaction with an alcohol are carried out on a desmycosin derivative (II') to produce Compound (XI). After effecting protection of the hydroxyl group at position 2' or the hydroxyl groups at positions 2' and 4' of Compound (XI) with an acetyl group or the like, a p-nitrobenzenesulfonyl halide is reacted to produce Compound (XII). A compound of the formula (1c) of the present invention is then prepared by removing the hydroxyl or aldehyde protective groups.

Protection of the hydroxyl group of Compound (XI) can be carried out according to the same method as described in Process (2). Reaction of Compound (XI) having a protected hydroxyl group and a p-nitrobenzenesulfonyl halide such as p-nitrobenzenesulfonyl chloride or p-nitrobenzenesulfonyl bromide is carried out in an organic solvent such as dichloromethane or pyridine in the presence of a tertiary amine such as pyridine, triethylamine, or the like. The reaction proceeds at a temperature below room temperature. Performing the reaction under ice-cooling is preferable.

Reaction of Compound (XII) and a di-lower alkyl amine is carried out using an excess amount of a di-lower alkyl amine in an inert organic solvent such as acetonitrile, dimethylformamide, or the like, usually, under heating.

Removal of the hydroxyl protective group of Compound (XIII) is carried out in the same manner as in Process (2), and of the aldehyde protective group in the same manner as in Process (1).

The compound of formula (I) of the present invention thus prepared may be, if necessary, purified by a separation-purification means conventionally used for macrolide antibiotics, such as column chromatography using an adsorbent such as silica gel, activated alumina, adsorption resin, or the like.

Hereinafter are presented experimental examples to illustrate the antimicrobial activity and infectious disease curing effect of the compound of formula (I). All compounds used in the experiments are those prepared in preparation examples hereinafter presented and the compounds are designated according to Preparation Example Nos. in which the same were prepared. These examples are given for illustration of the invention and are not intended to be limiting thereof.

EXPERIMENTAL EXAMPLES

Experimental Example 1 (Antimicrobial activity)

Minimum inhibitory concentrations (MIC, μg/ml) of various compounds of formula (I) against various microorganisms (about $10^6$/ml) were measured. The results are shown in Table 1.

TABLE 1

| (MIC, μg/ml) |
|---|
| Tested Compound |

TABLE 1-continued

| Tested Microorganism | (MIC, μg/ml) | | | | | | | | | | |
|---|---|---|---|---|---|---|---|---|---|---|---|
|  | 1 | 2 | 3 | 4 | 5 | 6 | 7 | 8 | 9 | 10 | 11 |
| *Staphylococcus aureus* FDA 209P JC-1 | 0.10 | 0.10 | 0.10 | 0.39 | 0.10 | 0.10 | 0.20 | 0.20 | 0.39 | 0.20 | 0.20 |
| *Staphylococcus aureus* MS 353 | 0.20 | 0.20 | 0.20 | 0.39 | 0.20 | 0.20 | 0.20 | 0.39 | 0.39 | 0.39 | 0.20 |
| *Staphylococcus aureus* MS 353 C36 | 0.20 | 0.10 | 0.20 | 0.39 | 0.20 | 0.20 | 0.20 | 0.39 | 0.78 | 0.39 | 0.39 |
| *Staphylococcus aureus* Smith | 0.39 | 0.20 | 0.39 | 0.78 | 0.39 | 0.39 | 0.78 | 0.78 | 0.78 | 0.78 | 0.78 |
| *Staphylococcus epidermidis* sp-al-1 | ≦0.05 | 0.10 | 0.20 | 0.39 | 0.20 | 0.10 | 0.20 | 0.39 | 0.78 | 0.78 | 0.39 |
| *Staphylococcus pyogenes* N.Y.5 | ≦0.05 | ≦0.05 | ≦0.05 | 0.10 | 0.05 | ≦0.05 | 0.20 | 0.10 | 0.20 | 0.10 | 0.10 |
| *Staphylococcus pyogenes* 1022 | — | >100 | >100 | >100 | 50 | — | >100 | >100 | >100 | >100 | 100 |
| *Staphylococcus pyogenes* S-23 | ≦0.05 | ≦0.05 | 0.10 | 0.20 | 0.10 | ≦0.05 | 0.20 | 0.10 | 0.20 | 0.39 | 0.20 |

| Tested Microorganism | Tested Compound | | | | | | | |
|---|---|---|---|---|---|---|---|---|
|  | 12 | 13 | 14 | 15 | 16 | 17 | 18 | Desmycosin |
| *Staphylococcus aureus* FDA 209P JC-1 | 0.20 | 0.20 | 0.20 | 0.39 | 0.78 | 0.39 | 0.20 | 0.20 |
| *Staphylococcus aureus* MS 353 | 0.20 | 0.20 | 0.20 | 0.39 | 0.39 | 0.39 | 0.20 | 0.20 |
| *Staphylococcus aureus* MS 353 C36 | 0.20 | 0.20 | 0.20 | 0.39 | 0.78 | 0.39 | 0.20 | 0.20 |
| *Staphylococcus aureus* Smith | 0.39 | 0.39 | 0.39 | 0.78 | 1.56 | 0.78 | 0.39 | 0.39 |
| *Staphylococcus epidermidis* sp-al-1 | 0.39 | 0.39 | 0.20 | 0.78 | 1.56 | 0.39 | 0.39 | 0.20 |
| *Staphylococcus pyogenes* N.Y.5 | 0.10 | 0.10 | 0.10 | ≦0.05 | 0.39 | 0.10 | 0.10 | ≦0.05 |
| *Staphylococcus pyogenes* 1022 | >100 | >100 | >100 | 50 | 50 | >100 | 100 | >100 |
| *Staphylococcus pyogenes* S-23 | 0.10 | 0.10 | ≦0.05 | 0.20 | 0.39 | 0.20 | 0.10 | ≦0.05 |

EXPERIMENTAL EXAMPLE 2

(Infectious disease curing effect)

A pre-incubated test microorganism, Staphylococcus pyogenes S-23, was suspended in a 5% mucin solution and inoculated into the ICR male mice (8 mice per group) abdomen in an amount of $2\times10^2$. After 1 hour, Compounds (I) of the present invention dissolved or suspended in a phosphate buffer were orally administered to the mice. The mice were inspected for 5 days to determine $ED_{50}$ (mg/kg) by the Van der Waerden method. The results are shown in Table 2.

TABLE 2

| Tested Compound | $ED_{50}$ (mg/kg) |
|---|---|
| 1 | 100–200 |
| 5 | 84 |
| 6 | 64.8 |
| 7 | 100–200 |
| 8 | 50 |
| Tylosin | >200 |
| 4'-Deoxydesmycosin | >200 |

The above results show that the Compounds (I) of the present invention possess an excellent antimicrobial activity and exhibit an outstanding infectious disease curing effect by oral administration.

Hereinafter are presented preparation examples of various compounds of formula (I). These examples are given for illustration of the invention and are not intended to be limiting thereof.

PREPARATION EXAMPLES

PREPARATION EXAMPLE 1

Preparation of 9-dihydro-9-O-methyldesmycosin [in formula (I), $R^1$=hydrogen, $R^2$=methyl, $R^3$=hydroxyl, X=—O— mycinose]

(1) To a solution of 5 g of desmycosin in 25 ml of methanol was added 1.48 g (1.2 equivalent) of p-toluenesulfonic acid and the mixture was stirred for 2 hours. After completion of the reaction, the reaction mixture was adjusted to pH 9–10 using 7% aqueous ammonia and extracted three times with 150 ml of chloroform. The organic layers collected were washed with saturated brine and the solvent was evaporated. The residue thus obtained was purified by column chromatography on silica gel (100 g; Art 9385, manufactured by Merck Co.) using a chloroformmethanol mixture (30:1–20:1) to collect the target fractions by a TLC, thus producing 5.2 g of desmycosin-20-dimethylacetal.

FAB-MS: 818(MH+), 786, 754

(2) To a solution of 3 g (3.67 mmol) of desmycosin-20-dimethylacetal prepared in (1) in 15 ml of methanol was added 0.55 g (4 equivalent) of sodium borohydride. The mixture was stirred at 0° C. for 1 hour. After completion of the reaction, the reaction mixture was adjusted to pH 9–10 using 7% aqueous ammonia and extracted with 100 ml of chloroform. The extract was washed with saturated brine, dehydrated with a Watman 1 PS filter, and dried under reduced pressure. The residue thus obtained was purified by column chromatography on silica gel (60 g; Art 9385, manufactured by Merck Co.), eluting with a linear gradient of chloroform-methanol (30:1 to 20:1) to collect the target fractions by confirmation with a TLC, thus producing 2.64 g of 9-dihydro-desmycosin-20-dimethylacetal.

FAB-MS: 820(MH+), 788

$UV\nu_{max}^{EtOH}$ 236 nm (3) To a solution of 2 g (2.44 mmol) of 9-dihydro-desmycosin-20-dimethylacetal prepared in (2) in 20 ml of methanol was added 1.5 ml (19.5 mmol) of trifluoroacetic acid. The mixture was stirred at room temperature for 6 hours. After the reaction, the reaction mixture was charged into ice-water and adjusted to pH 9–10 using 7% aqueous ammonia and extracted three times with 150 ml of chloroform. The organic layers were combined, washed with saturated brine, dehydrated with a Watman 1 PS filter, and dried under reduced pressure. The residue thus obtained was purified by column chromatography on silica gel (40 g; Art 9385, manufactured by Merck Co.), eluting with chloroform-methanol-concentrated aqueous ammonia (40:1:0.1) to collect the target fractions by confirmation with a TLC, thus producing 0.75 g of 9-dihydro-9-O-methyldesmycosin-20-dimethylacetal.

FAB-MS: 834(MH+)

NMR(CDCl$_3$) δ ppm: 1.74(s, 3H), 2.49(s, 6H), 3.22(s, 3H), 3.29(s, 3H), 3.36(s, 3H, 9-OMe), 3.49(s, 3H), 3.61(s, 3H), 4.31(d, 1 H), 4.52(d, 1 H), 4.96(d. t, 1 H ), 5.35(d, 1 H), 5.58(d. d, 1 H), 6.16(d, 1 H)

(4) To a solution of 0.6 g of 9-dihydro-9-O-methyldesmycosin-20-dimethylacetal prepared in (3) in of acetonitrile-water (3:2 by volume) was added 0.11 ml (2 equivalent) of trifluoroacetic acid. The mixture was stirred to react at room temperature for 45 minutes. After confirmation of the elimination of the raw material by TCL, the reaction mixture was adjusted to pH 9-10 using 7% aqueous ammonia and extracted three times with 150 ml of chloroform. The organic layers were combined, washed with saturated brine, dehydrated with a Watman 1 PS filter, and concentrated. The residue thus obtained was purified by column chromatography on silica gel (12 g; Art 9385, manufactured by Merck Co.), eluting with chloroform-methanol-concentrated aqueous ammonia (40:1:0.1) to produce 0.14 g of 9-dihydro-9-O-methyldesmycosin.

FAB-MS: 788(MH+)

UV$\nu_{max}^{EtOH}$ 236 nm

NMR(CDCl$_3$) δ ppm: 1.74(s, 3H), 2.50(s, 6H), 3.20(s, 3H, 9-OMe), 3.50(s, 3 H), 3.62(s,3 H), 4.32(d,1 H), 4.56(d, 1H), 4.98(d, t, 1H), 5.39(d, 1H), 5.56(d. d, 1H), 6.23(d, 1H), 9.75(s, 1H)

PREPARATION EXAMPLE 2

Preparation of 9-dihydro-9-O-ethyldesmycosin [in formula (I), $R^1$=hydrogen, $R^2$=ethyl, $R^3$=hydroxyl, X=—O— mycinose]

(1) The same procedure as in Preparation Example 1 (1) was carried out, except for using a solution of 10 g of desmycosin in 50 ml of ethanol, to produce 9.5 g of desmycosin-20-diethylacetal. FAB-MS: 846(MH+), 800, 754

(2) The same procedure as in Preparation Example 1 (2) was carried out, except for using 3 g of desmycosin-20-diethylacetal prepared in (1) and reacting for 2.5 hours, to produce 2.73 g of 9-dihydro-desmycosin-20-diethylacetal.

FAB-MS: 848(MH+)

(3) The same procedure as in Preparation Example 1 (3) was carried out, except for using a solution of 2 g of 9-dihydro-desmycosin-20-diethylacetal prepared in (2) in 20 ml of ethanol and reacting for 72 hours, to produce 0.4 g of 9-dihydro-9-O-ethyldesmycosin-20-diethylacetal.

FAB-MS: 876(MH+), 830, 784

NMR(CDCl$_3$) δ ppm: 1.72(s, 3H), 2.49(s, 6H), 3.48(s, 3H), 3.61(s, 3H), 4.32(d, 1H), 4.54(d, 1H), 4.91(d. t, 1H), 5.29(d, 1H), 5.59(d. d, 1H), 6.13(d, 1H)

(4) The same procedure as in Preparation Example 1 (4) was carried out, except for using 0.4 g of 9-dihydro-9-O-ethyldesmycosin-20-diethylacetal prepared in (3), to produce 90 mg of 9-dihydro-9-O-ethyldesmycosin.

FAB-MS: 802(MH+)

UV$\nu_{max}^{EtOH}$ 236 nm

NMR(CDCl$_3$) δ ppm: 1.73(s, 3H), 2.50(s, 6H), 3.50(s, 3H), 3.62(s, 3H), 4.33(d, 1H), 4.56 (d, 1H), 4.9 7(d. t, 1H), 5.35(d, 1H), 5.57(d. d, 1H), 6.18(d, 1H), 9.74(s, 1H).

PREPARATION EXAMPLE 3

Preparation of 9-dihydro-9-O-propyldesmycosin [in formula (I), $R^1$=hydrogen, $R^2$=propyl, $R^3$=hydroxyl, X=—O— mycinose]

(1) The same procedure as in Preparation Example 1 (1) was carried out, except for using a solution of 5 g of desmycosin in 25 ml of 1-propanol, to produce 4.8 g of desmycosin-20-dipropylacetal.

FAB-MS: 874(MH+), 814, 754

(2) The same procedure as in Preparation Example 1 (2) was carried out, except for using 3 g of desmycosin-20-dipropylacetal prepared in (1) and reacting for 30 minutes, to produce 2.58 g of 9-dihydro-desmycosin-20-dipropylacetal.

FAB-MS: 876(MH+), 816, 756

(3) The same procedure as in Preparation Example 1 (3) was carried out, except for using 2 g of 9-dihydro-desmycosin-20-dipropylacetal prepared in (2) and reacting for 96 hours, to produce 0.42 g of 9-dihydro-9-O-propyldesmycosin-20-dipropylacetal.

FAB-MS: 918(MH+), 850, 798

NMR(CDCl$_3$) δ ppm: 1.73(s, 3H), 2.49(s, 3H), 3.49(s, 3H), 3.61(s, 3H), 4.33(d, 1H), 4.55(d, 1H), 4.96(d. t, 1H), 5.30(d, 1H), 5.60(d. d, 1H), 6.12(d, 1H)

(4) The same procedure as in Preparation Example 1 (4) was carried out, except for using 0.42 g of 9-dihydro-9-O-propyldesmycosin-20-dipropylacetal prepared in (3), to produce 90 mg of 9-dihydro-9-O-propyldesmycosin.

FAB-MS: 816(MH+)

UV$\nu_{max}^{EtOH}$ 236 nm

NMR(CDCl$_3$) δ ppm: 1.72(s, 3H), 2.49(s, 6H), 3.49(s, 3H), 3.61(s, 3H), 4.33(d, 1H), 4.55(d, 1H), 4.96(d, 1H), 5.34(d, 1H), 5.54(d. d, 1H), 6.16(d, 1H), 9.74(s,1H)

PREPARATION EXAMPLE 4

Preparation of 9-dihydro-9-O-butyldesmycosin [in formula (I), $R^1$=hydrogen, $R^2$=butyl, $R^3$=hydroxyl, X=—O— mycinose]

(1) The same procedure as in Preparation Example 1 (1) was carried out, except for using a solution of 5 g of desmycosin in 25 ml of 1-butanol and reacting 17 hours, to produce 4.4 g of desmycosin-20-dibutylacetal.

FAB-MS: 902(MH+), 828, 754

(2) The same procedure as in Preparation Example 1 (2) was carried out, except for using 3 g of desmycosin-20-dibutylacetal prepared in (1), reacting for 30 minutes, and eluting column chromatography with chloroform-methanol-concentrated aqueous ammonia (40:1:0.1), to produce 2.37 g of 9-dihydro-desmycosin-20-dibutylacetal.

FAB-Mass: 904(MH+), 830, 756

(3) The same procedure as in Preparation Example 1 (3) was carried out, except for using 2 g of 9-dihydro-desmycosin-20-dibutylacetal prepared in (2) and reacting for 72 hours, to produce 0.64 g of 9-dihydro-9-O-butyl-desmycosin-20-dibutylacetal.

FAB-Mass: 960(MH+), 886

NMR(CDCl$_3$) δ ppm: 1.72(s, 3H), 2.50(s, 6H), 3.49(s, 3H), 3.61(s, 3H, 4.33(d, 1H), 4.55(d, 1H), 4.95(d. t, 1H), 5.31(d, 1H), 5.66(d. d, 1H), 6.12(d, 1H), (4) The same procedure as in Preparation Example 1 (4) was carried out, except for using 0.30 g of 9-dihydro-9-O-butyldesmycosin-20-dibutylacetal prepared in (3), to produce 0.18 g of 9-dihydro-9-O-butyldesmycosin.

FAB-Mass: 830(MH+)

UV$\nu_{max}^{EtOH}$ 236 nm

NMR(CDCl$_3$) δ ppm: 1.73(s, 3H, 2.49(s, 6H, 3.49(s, 3H), 3.61(s, 3H), 4.32(d, 1H), 4.55(d, 1H), 4.96(d. t, 1H), 5.35(d, 1H), 5.58(d. d, 1H), 6.15(d, 1H), 9.73(s, 1H)

PREPARATION EXAMPLE 5

Preparation of 9-dihydro-9-O-methyl-3-O-propionyldesmycosin [in formula (I), $R^1$=propionyl, $R^2$=methyl, $R^3$=hydroxyl, X=—O— mycinose]

(1) To a solution of 1.16 (1.4 mmol) of 3-O-propionyldesmycosin in 5 ml of methanol was added 320 mg (1.68 mmol) of p-toluenesulfonic acid and the mixture was stirred for 1 hour at room temperature. After confirming the reaction completion by a TLC, the reaction mixture was charged into 25 ml of chloroform. The mixture was washed twice with 25 ml of 7% aqueous ammonia and twice with 25 ml of saturated brine, passed through a Watman 1 PS filter, with the filtrate then being concentrated under reduced pressure to produce 1.11 g (12.7 mmol) of crude 3-O-propionyldesmycosin-20-dimethylacetal (yield: 90.7%).

(2) To a solution of 1.11 g (1.27 mmol) of 3-O-propionyldesmycosin-20-dimethylacetal prepared in (1) in 5 ml of methanol was added 190 mg (5.02 mmol) of sodium borohydride a bit at a time under ice-cooling. The mixture was reacted at 0–5° C. for 30 minutes while stirring. After the reaction, the reaction mixture was washed twice with 25 ml of 7% aqueous ammonia and twice with 25 ml of saturated brine, passed through a Watman 1 PS filter, with the filtrate then being concentrated under reduced pressure to produce 1.07 g (12.2 mmol) of crude 9-dihydro-3-O-propionyldesmycosin-20-dimethylacetal (yield: 96.1%).

(3) To a solution of 1.07 g (1.22 mmol) of 9-dihydro-3-O-propionyldesmycosin-20-dimethylacetal prepared in (2) in 5 ml of methanol was added 0.75 ml (9.76 mmol) of trifluoroacetic acid. The mixture was stirred at room temperature overnight. After the reaction, the reaction mixture was charged into 50 ml of 7% aqueous ammonia and extracted three times with 15 ml of chloroform. The chloroform layers were combined, washed once with 50 ml of 7% aqueous ammonia and twice with 50 ml of saturated brine, passed through a Watman 1 PS filter, and concentrated under reduced pressure. The residue thus obtained was purified by column chromatography on silica gel (20 g; Art 9385, manufactured by Merck Co.), eluting with chloroform-methanol-concentrated aqueous ammonia to collect the target fractions by confirmation with a TLC, thus producing 520 mg (0.58 mmol) of 9-dihydro-9-O-methyl-3-O-propionyldesmycosin-20-dimethylacetal (yield: 47.9%).

FAB-Mass 890(MH+)

NMR(CDCl$_3$) δ ppm:1.74(s, 3H, 2.49(s, 6H), 3.22(s, 3H), 3.29(s, 3H), 3.35(s, 3H), 3.46(s, 3H), 3.60(s, 3H), 4.25(d, 1H), 4.55(d, 1H), 4.66–5.00(m, 1H), 5.15(br. d, 1H), 5.42(d, 1H), 5.60(d. d, 1H), 6.40(d, 1H)

(4) To a solution of 520 mg (0.58 mmol) of 9-dihydro-9-O-methyl-3-O-propionyldesmycosin-20-dimethylacetal prepared in (3) in 7.5 ml of acetonitrile and 5 ml of water was added 0.25 ml of trifluoroacetic acid. The mixture was stirred to react at room temperature for 45 minutes. After the reaction, the reaction mixture was charged into 50 ml of 7% aqueous ammonia and extracted three times with 25 ml of chloroform. The chloroform layers were combined, washed once with 50 ml of 7% aqueous ammonia and twice with 50 ml of saturated brine, passed through a Watman 1 PS filter, and concentrated under reduced pressure. The residue thus obtained was purified by column chromatography on silica gel (10 g; Art 9385, manufactured by Merck Co.), eluting with chloroform-methanol-concentrated aqueous ammonia to collect the target fractions. The fractions were concentrated and purified by preparative HPLC (ODS-5, 20φ×250 mm column) eluting with phosphate buffer-methanol (35:65) to produce 200 mg (0.24 mmol) of 9-dihydro-9-O-methyl-3-O-propionyldesmycosin (yield:40.8%).

FAB-Mass:844(MH+)

NMR(CDCl$_3$) δ ppm:1.76(d, 3H), 2.49(s, 6H), 3.21(s, 3H, 9-OMe), 3.46(s, 3H), 3.60(s, 3H), 4.23(d, 1H), 4.55(d, 1H), 4.84(d. t, 1H), 5.21(d, 1H), 5.44(d. d, 1H), 5.48(d, 1H), 6.59(d, 1H), 9.68(s, 1H)

PREPARATION EXAMPLE 6

Preparation of 9-dihydro-9-O-methyl-4'-deoxydesmycosin [in formula (I), R$^1$=hydrogen, R$^2$=methyl, R$^3$=hydrogen, X=—O— mycinose]

(1) To a solution of 1.0 g of 4'-deoxydesmycosin in 10 ml of methanol was added 302 mg of p-toluenesulfonic acid (monohydrate) and the mixture was reacted at room temperature for 1 hour while stirring. After the reaction, the reaction mixture was charged into 100 ml of ice-cooled water, adjusted to pH 9–10 using 7% aqueous ammonia, and extracted two times with 50 ml of chloroform. The chloroform layers were combined, washed with saturated brine, passed through a Watman 1 PS filter, and concentrated under reduced pressure to produce crude 4'-deoxydesmycosin-20-dimethylacetal.

(2) The crude 4'-deoxydesmycosin-20-dimethylacetal prepared in (1) was dissolved into 10 ml of methanol, and 200 mg of sodium borohydride was added to the solution. The mixture was stirred at room temperature for 30 minutes. After the reaction, the reaction mixture was charged into 100 ml of water, and extracted two times with 50 ml of chloroform. The chloroform layers were combined, passed through a Watman 1 PS filter, and concentrated under reduced pressure to produce crude 9-dihydro-4'-deoxydesmycosin-20-dimethylacetal.

(3) To a solution of crude 9-dihydro-4'-deoxydesmycosin-20-dimethylacetal prepared in (2) in 10 ml of methanol was added 1 ml of trifluoroacetic acid. The mixture was stirred at room temperature for 72 hours. After the reaction, the reaction mixture was charged into 100 ml of ice-water, adjusted to pH 9–10 using 7% aqueous ammonia, and extracted two times with 50 ml of chloroform. The chloroform layers were combined, washed with saturated brine, passed through a Watman 1 PS filter, and dried under reduced pressure to produce 0.9 g of 9-dihydro-9-O-methyl-4'-deoxydesmycosin-20-dimethylacetal.

(4) To a solution of 0.9 g of 9-dihydro-9-O-methyl-4'-deoxydesmycosin-20-dimethylacetal prepared in (3) in 25 ml of acetonitrile-water (3:2 by volume) was added 1 ml of trifluoroacetic acid. The mixture was stirred to react at room temperature for 1.5 hours. After the reaction, the reaction mixture was adjusted to pH 9–10 using 7% aqueous ammonia and extracted twice with 50 ml of chloroform. The chloroform layers were combined, washed with saturated brine, dehydrated with a Watman 1 PS filter, and dried under reduced pressure. The residue thus produced was purified by column chromatography using 30 g of silica gel (Art 9385; manufactured by Merck Co.), eluting with a gradient of chloroform-methanol-concentrated aqueous ammonia (50:1:0.1 to 30:1:0.1) to produce 186 mg of 9-dihydro-9-O-methyl-4'-deoxydesmycosin.

FAB-Mass:722(MH+), 158

UV$\nu_{max}^{EtOH}$ 236 nm

NMR(CDCl$_3$) δ ppm:1.73(s, 3H, 2.27(s, 6H), 3.18(s, 3H, 9-OMe), 3.49(s, 3H), 3.61 (s, 3H, 4.28(d, 1H), 4.56(d, 1H), 4.97(d. t, 1H), 5.41(d, 1H), 5.48(d. d, 1H), 6.26(d, 1H), 9.82(s, 1H)

PREPARATION EXAMPLE 7

Preparation of 9-dihydro-9-O-methyl-23-demycinosyloxy-23-dimethylamino-4'-deoxydesmycosin [in form hydrogen, $R^2$=methyl, $R^3$=hydrogen, X=dimethylamino]

(1) To a solution of 0.5 g (0.8 mmol) of 23-demycinosyl-4'-deoxydesmycosin-20-dimethylacetal in 15 ml of ethanol-methanol (1:1) was added under ice-cooling 122 mg of sodium borohydride. The mixture was reacted at room temperature for 1 hour while stirring. After the reaction, water was added to the reaction mixture. The mixture was extracted with chloroform. The extract was washed with water, passed through a Watman 1 PS filter, and concentrated under reduced pressure to produce 0.45 g of 9-dihydro-23-demycinosyl-4'-deoxydesmycosin-20-dimethylacetal.

(2) A solution of 0.45 g of 9-dihydro-23-demycinosyl-4'-deoxydesmycosin-20-dimethylacetal prepared in (1) in 5 ml of methanol was added under ice-cooling 0.5 ml of trifluoroacetic acid. The mixture was stirred at room temperature for 56 hours. After the reaction, the reaction mixture was adjusted to pH 8-9 with 7% aqueous ammonia under ice-cooling, extracted with chloroform. The extract was washed with water, passed through a Watman 1 PS filter, and concentrated under reduced pressure to produce 0.51 g of crude 9-dihydro-9-O-methyl-23-demycinosyl-4'-deoxy-desmycosin-20-dimethylacetal. This crude product was purified by column chromatography on silica gel (Art 7734; manufactured by Merck Co.), eluting with chloroform-methanol (30:1) to produce 0.18 g of a purified product.

(3) To a solution of the 9-dihydro-9-O-methyl-23-demycinosyl-4'-deoxydesmycosin-20-dimethylacetal prepared in (2) in 3 ml of dichloromethane was added 0.053 ml of acetic anhydride. The mixture was reacted for 1.5 hours while stirring. After the reaction, the reaction mixture was poured into water and adjusted to pH 8-9 using 7% aqueous ammonia under cooling and extracted with chloroform. The extract was washed with water, passed through a Watman 1 PS filter, and dried under reduced pressure to produce 0.16 g of a 2'-acetyl compound. To the compound was added 103 mg of p-nitro-benzenesulfonyl chloride and the mixture was reacted under ice-cooling for 3 hours while stirring. After the reaction, the reaction mixture was charged into cold saturated brine-aqueous ammonia to collect the deposited slurry by filtration. The slurry was dissolved into chloroform, washed with aqueous ammonia, passed through a Watman 1 PS filter, and dried under reduced pressure to produce 0.18 g of crude 2'-O-acetyl-9-dihydro-9-O-methyl-23-demycinosyl-23-O-p-nitrobenzenesulfonyl-4-deoxy-purified by column chromatography using 5.4 g of silica gel (Art 7734; manufactured by Merck Co.), eluting with benzene-acetone (4:1) to produce 0.17 g of a purified product.

(4) The purified 2'-O-acetyl-9-dihydro-9-O-methyl-23-demycinosyl-23-O-p-nitrobenzenesufonyl-4'-deoxydesmycosin-20-dimethylacetal (0.17 g) prepared in (3) was dissolved into 10 ml of acetonitrile. Dimethylamine gas was bubbled at room temperature into the solution until saturation occurred, followed by stirring at 50° C. for 30 minutes. The resultant reaction mixture was concentrated, and the residue was dissolved in chloroform, washed with water, passed through a Watman 1 PS filter, and dried under reduced pressure to produce 0.10 g of 2,'-O-acetyl-9-dihydro-9-O-methyl-23-demycinosyloxy-23-dimethylamino-4'-deoxydesmycosin-20-dimethylacetal. The product was dissolved into 3 ml of methanol and heated at 50° C. for 14 hours while stirring. The resulting reaction mixture was concentrated, and the residue was dissolved into chloroform, adjusted to pH 8-9 with aqueous ammonia, and extracted with chloroform. The extract was washed with water, passed through a Watman 1 PS filter, and dried under reduced pressure to produce 0.08 g of a deacetylated compound. To this compound were added 2.67 ml of acetonitrile, 2.0 ml of water, and 0.1 ml of trifluoroacetic acid. The mixture was reacted at room temperature for 15 minutes while stirring. After an addition of aqueous ammonia under cooling to adjust the pH to 8-9, the resultant mixture was extracted with chloroform. The extract was washed with water, passed through a Watman 1 PS filter, and dried under reduced pressure to produce 0.08 g of crude 9-dihydro-9-O-methyl-23-demycinosyloxy-23-dimethylamino-4'-deoxydesmycosin. The crude product was subjected to column chromatography using 4 g of silica gel (Art 7734; manufactured by Merck Co.), eluting with chloroform-methanol (30:1) to produce 57 mg of purified title compound.

Cl-Mass:625(MH+), 670(MH+-18), 176, 158

NMR(CDCl$_3$) δ ppm:1.77(s, 3 H), 2.19(s, 6 H), 2.29(s, 6 H), 3.20(s, 3 H, 9-OMe), 4.30(d, 1H), 4.71(d. t, 1H), 5.25(d, 1H), 5.50(d. d, 1H), 6.27(d, 1H), 9.79(s, 1H),

PREPARATION EXAMPLE 8

Preparation of 9-dihydro-9-O-ethyl-3-O-acetyldesmycosin [in formula (I), $R^1$=acetyl, $R^2$=ethyl, $R^3$=hydroxyl, X=—O—mycinose]

(1) To a solution of 1.76 g (2.01 mmol) of 9-O-ethyl-9-dihydrodesmycosin-20-diethylacetal in 10 ml of pyridine were added 2.6 ml (27.6 mmol) of acetic anhydride and 0.02 g (0.16 mmol) of dimethylamino pyridine. The mixture was reacted at 60° C. for 15.5 hours while stirring. After confirming termination of the reaction by a TLC, the resultant reaction mixture was alkalinized by an addition of 7 ml of 7% aqueous ammonia, extracted three times with 150 ml of 7% aqueous ammonia and three times with 150 ml of saturated brine, passed through a Watman 1 PS filter, and concentrated under reduced pressure. The residue thus produced was purified by column chromatography using 35 g of silica gel (Art 7734; manufactured by Merck Co.), eluting gradiently with toluene→toluene-acetone (30:1→20:1→10:1→7:1) to collect the target fraction, thus producing 1.50 g (1.44 mmol) of 9-O-ethyl-3,2',4',4"-tetra-O-acetyl-9-dihydrodesmycosin-20-diethylacetal (yield:71.5%).

NMR(CDCl$_3$) δ ppm:1.72(s, 3H), 2.03(s, 3H), 2.05(s, 3H), 2.38(s, 6H), 2.51(s, 6H), 3.44(s, 3H), 3.51(s, 3H), 4.34(d, 1H, 7 Hz), 4.53(d, 1H, 8 Hz), 4.91-5.16(m, 1H), 5.32(d, 1H, 8 Hz), 5.60(d. d, 1H, 8 Hz, 16 Hz), 6.26(d, 1H, 16 Hz)

FAB-Mass:1044(MH+)

(2) The 9-O-ethyl-3,2',4',4"-tetra-O-acetyl-9-dihydrodesmycosin-20-diethylacetal (1.50 g, 1.44 mmol) prepared in (1) was dissolved into 15 ml of methanol, and the solution was stirred at 55° C. for 5 hours. After confirming termination of the reaction by a TLC, the resultant reaction mixture was alkalinized with an addition of 5 ml of 7% aqueous ammonia and extracted three times with 100 ml of chloroform. The extract was washed three times with 150 ml of 7% aqueous ammonia and three times with 150 ml of saturated brine, passed through a Watman 1 PS filter, and concentrated under reduced pressure to produce 1.33 g (1.38 mmol) of 9-O-ethyl-3,4''-di-O-acetyl-9-dihydrodesmycosin-20-diethylacetal (yield:96.2%).

NMR(CDCl$_3$) δ ppm:1.74(s, 3H), 2.06(s, 3H), 2.49(s, 6H), 3.46(s, 3H), 3.54(s, 3H), 4.23(d, 1H, 7 Hz), 4.54(d, 1H, 8 Hz), 4.99–5.22(m, 1H), 5.34(d, 1H, 8 Hz), 5.59(d. d, 1H, 8 Hz, 16 Hz), 6.28(d, 1H, 16 Hz), 6.28(d, 1H, 16 Hz)

FAB-Mass:960(MH+)

(3) The 9-O-ethyl-3,4''-di-O-acetyl-9-dihydrodesmycosin-20-diethylacetal (1.33 g, 1.38 mmol) prepared in (2) was dissolved into 5 ml of methanol and 1 ml of triethylamine, and 1 ml of water, and the solution was stirred at room temperature for 21 hours. The resultant reaction mixture extracted three times with 100 ml of chloroform after the addition of 5 ml of 7% aqueous ammonia. The extract was washed three times with 150 ml of 7% aqueous ammonia and three times with 150 ml of saturated brine, passed through a Watman 1 PS filter, and concentrated under reduced pressure. The residue thus produced was purified by column chromatography using 30 g of silica gel (Art 9385; manufactured by Merck Co.), eluting gradiently with chloroform→chloroform-methanol-concentrated aqueous ammonia (60:1:0.1) to collect the target fraction, thus producing 734 mg (0.80 mmol) of 9-O-ethyl-3-O-acetyl-9-dihydrodesmycosin-20-diethylacetal (yield:57.8%).

NMR(CDCl$_3$) δ ppm:1.73(s, 3H), 2.08(s, 3H), 2.49(s, 6H), 3.46(s, 3H), 3.60(s, 3H), 4.22(d, 1H, 7 Hz), 4.54(d, 1 H, 8 Hz), 4.96–5.20(m, 1H), 5.56(d. d, 1H, 8 Hz 16 Hz), 6.25(d, 1H, 16 Hz)

FAB-Mass:918(MH+)

(4) The 9-O-ethyl-3-O-acetyl-9-dihydrodesmycosin-20-diethylacetal (177.9 mg, 0.194 mmol) prepared in (3) was dissolved into 3 ml of acetonitrile and 2 ml of water. To the solution was added 0.030 ml (0.39 mmol) of trifluoroacetic acid and the mixture was stirred at room temperature for 45 minutes. After confirming termination of the reaction by a TLC, the resultant reaction mixture was alkalinized with an addition of 3 ml of 7% aqueous ammonia and extracted three times with 30 ml of chloroform. The extract was washed three times with 50 ml of 7% aqueous ammonia and three times with 50 ml of saturated brine, passed through a Watman 1 PS filter, and concentrated under reduced pressure. The residue was purified by column chromatography using 5 g of silica gel (Art 9385; manufactured by Merck Co.), eluting gradiently with chloroform→chloroform-methanol (30:1→20:1→10:1) to collect the target fraction, thus producing 106.4 mg (0.13 mmol) of 9-O-ethyl-3-O-acetyl-9-dihydrodesmycosin (yield:64.9%).

NMR(CDCl$_3$) δ ppm:1.76(s, 3H), 2.21(s, 3H), 2.50(s, 6H), 3.45(s, 3H), 3.60(s, 3H), 4.24(d, 1H), 7 Hz), 4.55(d, 1H, 8 Hz), 4.82–4.87(m, 1H), 5.20(d, 1H, 8 Hz), 5.48(d. d, 1H, 8 Hz, 16 Hz), 6.56(d, 1H, 16 Hz), 9.70(s, 1H)

FAB-Mass:844(MH+)
FAB-Mass:844(MH+)

PREPARATION EXAMPLE 9

Preparation of 9-dihydro-9--O-propyl-3-O-acetyldesmycosin [in formula (I), $R^1$=acetyl, $R^2$=propyl, $R^3$=hydroxyl, X=—O— mycinose]

(1) To a solution of 2 g (2.18 mmol) of 9-O-propyl-9-dihydrodesmycosin-20-dipropylacetal in 10 ml of pyridine were added 2.47 ml (26.1 mmol) of acetic anhydride and 0.03 g (0.24 mmol) of dimethylaminopyridine. The mixture was reacted at 60° C. for 15.5 hours while stirring. After confirming termination of the reaction by a TLC, the resultant reaction mixture was alkalinized with an addition of 7 ml of 7% aqueous ammonia, extracted three times with 100 ml of chloroform. The extract was washed three times with 150 ml of 7% aqueous ammonia and three times with 150 ml of saturated brine, passed through a Watman 1 PS filter, and concentrated under reduced pressure. The residue was purified by column chromatography using 40 g of silica gel (Art 7734; manufactured by Merck Co.), eluting gradiently with toluene→toluene-acetone (30:1→20:1→10:1→7:1) to collect the target fraction, thus producing 1.40 g (1.29 mmol) of 9-O-propyl-3,2',4',4''-tetra-O-acetyl-9-dihydrodesmycosin-20-dipropylacetal (yield:59.2%)

NMR(CDCl$_3$) δ ppm:1.71(s, 3H), 2.04(s, 3H), 2.05(s, 3H), 2.11(s, 6H), 2.33(s, 6H), 3.45(s, 3H), 3.51(s, 3H), 4.35(d, 1H), 7 Hz), 4.60(d, 1H, 8 Hz), 4.92–5.16(m, 1H), 5.29(d, 1H, 8 Hz), 5.52(d. d, 1H, 8 Hz, 16 Hz), 6.24(d, 1H, 16 Hz)

FAB-Mass:1086(MH+)

(2) The 9-O-propyl-3,2',4',4''-tetra-O-acetyl-9-dihydrodesmycosin-20-dipropylacetal (1.1 g, 1.01 mmol) prepared in (1) was dissolved into 12 ml of methanol, and the solution was stirred at 55° C. for 5 hours. After confirming termination of the reaction by a TLC, the resultant reaction mixture was alkalinized with an addition of 5 ml of 7% aqueous ammonia and extracted three times with 100 ml of chloroform. The extract was washed three times with 150 ml of 7% aqueous ammonia and three times with 150 ml of saturated brine, passed through a Watman 1 PS filter, and concentrated under reduced pressure. The residue was purified by column chromatography using 2.4 g of silica gel (Art 9385; manufactured by Merck Co.), eluting gradiently with chloroform→chloroform-methanol-concentrated aqueous ammonia (80:1:0.1) to collect the target fraction, thus producing 952.6 mg (0.95 mmol) of 9-O-propyl-3,4''-di-O -acetyl-9-dihydrodesmycosin-20-dipropylacetal (yield: 94.1%).

NMR(CDCl$_3$) δ ppm: 1.73(s, 3H), 2.08(s, 3H), 2.11(s, 3H), 2.48(s, 6H), 3.45(s, 3H), 3.52(s, 3H), 4.23(d, 1H, 7 Hz), 4.61(d, 1H, 8 Hz), 5.02–5.16(m, 1H), 5.35(d, 1H, 10 Hz), 5.55(d. d, 1H, 8 Hz, 16 Hz), 6.27(d, 1H, 16 Hz)

(3) The 9-O-propyl-3,4''-di-O-acetyl-9-dihydrodesmycosin-20-dipropylacetal (952.6 mg, 0.95 mmol) prepared in (2) was dissolved into 10 ml of methanol and 2 ml of triethylamine, and the solution was stirred at room temperature for 15 hours. The resultant reaction mixture was extracted three times with 100 ml of chloroform after the addition of 5 ml of 7% aqueous ammonia. The extract was washed three times with 150 ml of 7% aqueous ammonia and three times with 150 ml of saturated brine, passed through a Watman 1 PS filter, and concentrated under reduced pressure to produce 935.2 mg (0.974 mmol) of 9-O-propyl-3-O-acetyl-9-dihydrodesmycosin-20-dipropylacetal (yield: 102.5%).

NMR(CDCl$_3$) δ ppm: 1.73(s, 3H), 2.08(s, 3H), 2.48(s, 6H), 3.46(s, 3H), 3.60(s, 3H), 4.22(d, 1H, 7 Hz), 4.54(d, 1H, 8 Hz), 4.97–5.97(m, 1H), 5.35(d, 1H, 11 Hz), 5.59(d. d, 1H, 8 Hz, 16 Hz), 6.25(d, 1H, 16 Hz)

(4) The 9-O-propyl-3-O-acetyl-9-dihydrodesmycosin-20-dipropylacetal (885.3 mg, 0.92 mmol) prepared in (3) was dissolved into 15 ml of acetonitrile and 10 ml of water. To the solution was added 0.15 ml (1.95 mmol) of acetic anhydride and the mixture was stirred at room temperature for 30 minutes. After confirming termination of the reaction by a TLC, the resultant reaction mixture was alkalinized with an addition of 5 ml of 7% aqueous ammonia and extracted three times with 100 ml of chloroform. The extract was washed three times with 150 ml of 7% aqueous ammonia and three times with 150 ml of saturated brine, passed through a Watman 1 PS filter, and concentrated under reduced pressure. The residue was purified by column chromatography using 18 g of silica gel (Art 9385; manufactured by Merck Co.), eluting gradiently with chloroform→chloroform-methanol-concentrated aqueous ammonia (70:1:0.1→60:1:0.1→50:1:0.1) to collect the target fraction, thus producing 498.4 mg (0.58 mmol) of 9-O-propyl-3-O-acetyl-9-dihydrodesmycosin (yield: 63.1%). NMR(CDCl$_3$) δ ppm: 1.75(s, 3H), 2.21(s, 3H), 2.50(s, 6H), 3.45(s, 3H), 3.60(s, 3H), 4.23(d, 1H, 7 Hz), 4.54(d, 1H, 8 Hz), 4.55(d, 1H, 8 Hz), 4.81–4.87(m, 1H), 5.46(d. d, 1H, 8 Hz, 16 Hz), 6.54(d, 1H, 16 Hz), 9.78(s, 1H)

PREPARATION EXAMPLE 10

Preparation of
9-dihydro-9-O-ethyl-3-O-propionyldesmycosin [in formula (I), $R^1$=propionyl group, $R^2$=ethyl group, $R^3$=hydroxyl group, X=—O— mycinose]

(1) 4.18 g (4.77 mmol) of 9-O-ethyl-9-dihydrodesmycosin diethylacetal was dissolved in 20 ml of methylene chloride. 3.88 ml (41.1 mmol) of acetic anhydride and 0.66 g (5.4 mmol) of dimethylaminopyridine were added to the solution and the mixture was stirred for 15.5 hours at room temperature. After confirming the completion of the reaction by a thin layer chromatography, the reaction mixture was alkalinized using 10 ml of 7% aqueous ammonia and extracted three times with 100 ml of chloroform. The extract was washed three times with 500 ml of 7% aqueous ammonia and 500 ml of saturated brine, passed through a Watman 1 PS filter, and concentrated under reduced pressure. The residue thus produced was purified by a column chromatography on a silica gel (Art 7734, manufactured by Merck Co.) weighing 84 g, eluting with toluene and a gradient of toluene and toluene-acetone (100:1–70:1–50:1–30:1) to collect the target fractions, thus producing 4.13 g (4.12 mmol) of 9-O-ethyl-2',4',4''-tri-O-acetyl-9-dihydrodesmycosin-20-diethyl-acetal at a 86.3% yield.

NMR (CDCl$_3$) δ ppm: 1.72(s, 3H), 2.02(s, 3H), 2.05(s, 3H), 2.11(s, 3H), 2.33(s, 6H, 3.45(s, 3H), 3.52(s, 3H), 4.46(d, 1H, 7 Hz), 4.62(d, 1H, 8 Hz), 5.29(d, 1H, 8 Hz), 5.53(d. d, 1H, 8 Hz, 16 Hz), 6.17(d, 1H, 16 Hz).

(2) 4.13 g (4.12 mmol) of 9-O-ethyl-2',4',4''-tri-O-acetyl-9-dihydrodesmycosin-20-diethylacetal prepared in (1) was dissolved in 25 ml of pyridine. 1.81 ml (14.1 mmol) of anhydrous propionic acid and 0.058 g (0.47 mmol) of dimethylaminopyridine were added to the solution and the mixture was stirred for 14 hours at 60° C. After confirming the completion of the reaction by a thin layer chromatography, the reaction mixture was alkalinized using 10 ml of 7% aqueous ammonia and extracted three times with 100 ml of chloroform. The extract was washed three times with 500 ml of 7% aqueous ammonia and 500 ml of saturated brine, passed through a Watman 1 PS filter, and concentrated under reduced pressure. The residue thus produced was purified by a column chromatography on a silica gel (Art 7734, manufactured by Merck Co.) weighing 82 g, eluting with toluene and a gradient of toluene and toluene-acetone (30:1–20:1–10:1–7:1) to collect the target fractions, thus producing 3.36 g (3.17 mmol) of 9-O-ethyl-2',4',4''-tri-O-acetyl-3-O-propionyl-9-dihydrodesmycosin-20-diethylacetal at a 77.0% yield.

NMR (CDCl$_3$) δ ppm 1.72(s, 3H), 2.03(s, 3H), 2.06(s, 3H), 2.11(s, 1H), 2.33(s, 6H), 3.45(s, 3H), 3.52(s, 3H), 4.30(d, 1H, 7 Hz), 4.61(d, 1H, 8 Hz), 4.92–5.16(m, 1H), 5.28(d, 1H, 10 Hz), 5.50(d. d, 1H, 8 Hz, 16 Hz), 6.25(d, 1H, 16 Hz)

(3) 3.35 g (3.17 mmol) of 9-O-ethyl-2',4',4''-tri-O-acetyl- 3-O-propionyl-9-dihydrodesmycosin-20-diethylacetal prepared in (2) was dissolved in 50 ml of methanol, and the solution was stirred for 13 hours at 55° C. After confirming the completion of the reaction by a thin layer chromatography, the reaction mixture was alkalinized using 10 ml of a 7% aqueous ammonia and extracted three times with 300 ml of chloroform. The extract was washed three times with 300 ml of 7% aqueous ammonia and 300 ml of saturated brine, passed through a Watman 1 PS filter, and concentrated under reduced pressure. The residue thus produced was purified by a column chromatography on a silica gel (Art 9385, manufactured by Merck Co.) weighing 60 g, eluting with a gradient of chloroform and chloroform-methanol-concentrated aqueous ammonia (60:1:0.1) to collect the target fractions, thus producing 2.02 g (2.07 mmol) of 9-O-ethyl-4''-O-acetyl-3-O-propionyl-9-dihydrodesmycosin-20-diethylacetal at a 65.4% yield.

NMR (CDCl$_3$) δ ppm 1.73(s, 3H), 2.11(s, 3H), 2.49(s, 6H), 3.45(s, 3H), 3.51(s, 3H), 4.22(d, 1H, 7 Hz), 4.60(d, 1H, 8 Hz), 4.99–5.20(m, 1H), 5.30(d, 1H, 10 Hz), 5.51(d. d, 1H, 8 Hz, 16 Hz), 6.26(d, 1H, 16 Hz)

(4) 1.94 g (1.99 mmol) of 9-O-ethyl-4''-O-acetyl-3-O-propionyl-9-dihydrodesmycosin-20-diethylacetal prepared in (3) was dissolved in a mixed solution of 7.5 ml of methanol, 1.5 ml of water, and 1.5 ml of triethylamine and the mixture was stirred for 28.5 hours at room temperature. After confirming the completion of the reaction by a thin layer chromatography, the reaction mixture was poured into water and extracted three times with 100 ml of chloroform. The extract was washed three times with 300 ml of 7% aqueous ammonia and 300 ml of saturated brine, passed through a Watman 1 PS filter, and concentrated under reduced pressure. The residue thus produced was purified by a column chromatography on a silica gel (Art 9385, manufactured by Merck Co.) weighing 50 g, eluting with a gradient of chloroform and chloroform-methanol-concentrated aqueous ammonia (60:1:0.1) to collect the target fractions, thus producing 1.11 g (1.19 mmol) of 9-O-ethyl-3-O-propionyl-9-dihydrodesmycosin-20-diethylacetal at a 59.8% yield.

NMR (CDCl$_3$) δ ppm 1.73(s, 3H), 2.51(s, 6H), 3.46(s, 3H), 3.60(s, 3H), 4.23(d, 1H, 7 Hz), 4.54(d, 1H, 8 Hz), 4.99–5.21(m, 1H), 5.32(d, 1H, 9 Hz), 5.50(d. d, 1H, 8 Hz, 16 Hz), 6.26(d, 1H, 16 Hz).

(5) 1.10 g (1.18 mmol) of 9-O-ethyl-3-O-propionyl-9-dihydrodesmycosin-20-diethylacetal prepared in (4) was dissolved in a mixed solution of 17 ml of acetonitrile and 11.1 ml of water. To the solution was added 0.183 ml (2.38 mmol) of trifluoro acetic acid and the mixture was stirred for 45 minutes at room temperature. After confirming the completion of the reaction by a thin layer chromatography, the reaction mixture was alkalinized using 5 ml of 7% aqueous ammonia and extracted three times with 100 ml of chloroform. The extract was washed three times with 300 ml of 7% aqueous ammonia and 300 ml of saturated brine, passed through a Watman 1 PS filter, and concentrated under reduced pressure. The residue thus produced was purified by a column chromatography on a silica gel (Art 9385, manufactured by Merck Co.) weighing 25 g, eluting with a gradient of chloroform and chloroform-methanol-concentrated aqueous ammonia (40:1:0.1) to collect the target fractions, thus producing 230.1 mg (0.268 mmol) of 9-O-ethyl-3-O-propionyl-9-dihydrodesmycosin at a 22.7% yield.

NMR (CDCl$_3$) δ ppm 1.75(s, 3H), 2.50(s, 6H), 3.46(s, 3H), 3.60(s, 3H), 4.23(d, 1H, 7 Hz), 4.54(d, 1H, 8 Hz), 4.81–4.86(m, 1H), 5.21(d, 1H, 9 Hz), 5.49(d. d, 1H, 8 Hz, 16 Hz), 6.52(d, 1H, 16 Hz), 9.68(s, 1H).

PREPARATION EXAMPLE 11

Preparation of
9-dihydro-9-O-propyl-3-O-propionyldesmycosin [in formula (I), R$^1$=propionyl group, R$^2$=propyl group, R$^3$=hydroxyl group, X=—O— mycinose]

(1) 1.27 g (1.38 mmol) of 9-O-propyl-9-dihydrodesmycosin-20-dipropylacetal was dissolved in 7 ml of methylene chloride. 1.4 ml (14.8 mmol) of acetic anhydride and 16.7 mg (0.14 mmol) of dimethylaminopyridine were added to the solution and the mixture was stirred for 15 hours at room temperature. After confirming the completion of the reaction by a thin layer chromatography, the reaction mixture was alkalinized using 3 ml of 7% aqueous ammonia and extracted three times with 50 ml of chloroform. The extract was washed three times with 100 ml of 7% aqueous ammonia and 100 ml of saturated brine, passed through a Watman 1 PS filter, and concentrated under reduced pressure to produce 1.62 g (1.55 mmol) of 9-O-propyl-2',4',4''-tri-O-acetyl-9-dihydrodesmycosin-20-dipropylacetal at a 112% yield.

NMR (CDCl$_3$) δ ppm: 1.72(s, 3H), 2.02(s, 3H), 2.05(s, 3H), 2.11(s, 3H), 2.33(s, 6H), 3.46(s, 3H), 3.52(s, 3H), 4.31(d, 1H, 7 Hz), 4.56(d, 1H, 8 Hz), 5.46–5.68(m, 1H), 6.14(d. d, 1H, 8 Hz, 16 Hz), 6.45(d, 1H, 16 Hz)

(2) 1.62 g (1.55 mmol) of 9-O-propyl-2',4',4''-tri-O-acetyl-9-dihydrodesmycosin-20-dipropylacetal prepared in (1) was dissolved in 8.1 ml of pyridine. 0.60 ml (4.7 mmol) of anhydrous propionic acid and 0.02 g (0.16 mmol) of dimethylaminopyridine were added to the solution and the mixture was stirred for 6 hours at 60° C. After confirming the completion of the reaction by a thin layer chromatography, the reaction mixture was added dropwise to a mixture of 150 ml of water, 8 ml of 7% aqueous ammonia, and 8 ml of saturated brine. The precipitate thus produced was extracted three times with 50 ml of chloroform. The extract was washed three times with 100 ml of 7% aqueous ammonia and 100 ml of saturated brine, passed through a Watman 1 PS filter, and concentrated under reduced pressure. The residue thus produced was purified by a column chromatography on a silica gel (Art 7734, manufactured by Merck Co.) weighing 40 g, eluting with a gradient of toluene and toluene-acetone (30:1–20:1–10:1) to collect the target fractions, thus producing 902.8 mg (0.82 mmol) of 9-O-propyl-2',4',4''-tri-O-acetyl-3-O-propionyl-9-dihydrodesmycosin-20-dipropylacetal at a 52.9% yield.

NMR (CDCl$_3$) δ ppm: 1.72(s, 3H), 2.03(s, 3H), 2.06(s, 3H), 2.11(s, 3H), 2.33(s, 6H), 3.46(s, 3H), 3.52(s, 3H), 4.35(d, 1H, 7 Hz), 4.61(d, 1H, 8 Hz), 4.96–5.12(m, 1H), 5.47(d. d, 1H, 8 Hz, 16 Hz), 6.23(d, 1H, 16 Hz)

(3) 902.8 mg (0.82 mmol) of 9-O-propyl-2',4',4''-tri-O-acetyl-3-O-propionyl-9-dihydrodesmycosin-20-dipropylacetal prepared in (2) was dissolved in 10 ml of methanol, and the solution was stirred for 7 hours at 55° C. After confirming the completion of the reaction by a thin layer chromatography, the reaction mixture was alkalinized using 5 ml of 7% aqueous ammonia and extracted three times with 100 ml of chloroform. The extract was washed three times with 150 ml of 7% aqueous ammonia and 150 ml of saturated brine, passed through a Watman 1 PS filter, and concentrated under reduced pressure. The residue thus produced was purified by a column chromatography on a silica gel (Art 9385, manufactured by Merck Co.) weighing 2.0 g, eluting with a gradient of chloroform and chloroform-methanol-concentrated aqueous ammonia (80:1:0.1) to collect the target fractions, thus producing 671.8 mg (0.66 mmol) of 9-O-propyl-4''-O-acetyl-3-O-propionyl-9-dihydrodesmycosin-20-dipropylacetal at a 80.5% yield.

NMR (CDCl$_3$) δ ppm 1.73(s, 3H), 2.11(s, 3H), 2.48(s, 6H), 3.45(s, 3H), 3.52(s, 3H), 4.22(d, 1H, 7 Hz), 4.60(d, 1H, 8 Hz), 4.96–5.20(m, 1H), 5.52(d. d, 1H, 8 Hz, 16 Hz), 6.10(d, 1H, 16 Hz)

(4) 671.8 mg (0.66 mmol) of 9-O-propyl-4''-O-acetyl-3-O-propionyl-9-dihydrodesmycosin-20-dipropylacetal prepared in (3) was dissolved in a mixed solution of 5 ml of methanol, 1 ml of water, and 1 ml of triethylamine and the mixture was stirred for 0.5 hour at room temperature. After confirming the completion of the reaction by a thin layer chromatography, the reaction mixture was poured into water and extracted three times with 100 ml of chloroform. The extract was washed three times with 150 ml of 7% aqueous ammonia and 50 ml of saturated brine, passed through a Watman 1 PS filter, and concentrated under reduced pressure. The residue thus produced was purified by a column chromatography on a silica gel (Art 9385, manufactured by Merck Co.) weighing 20 g, eluting with a gradient of chloroform and chloroform-methanol-concentrated aqueous ammonia (60:1:0.1) to collect the target fractions, thus producing 175.8 mg (0.180 mmol) of 9-O-propyl-3-O-propionyl-9-dihydrodesmycosin-20-dipropylacetal at a 27.3% yield.

NMR (CDCl$_3$) δ ppm 1.72(s, 3H), 2.48(s, 6H), 3.46(s, 3H), 3.60(s, 3H), 4.22(d, 1H, 7 Hz), 4.54(d, 1H, 8 Hz), 4.99–5.16(m, 1H), 5.35(d, 1H, 8 Hz), 5.48(d. d, 1H, 8 Hz, 16 Hz), 6.25(d, 1H, 16 Hz)

(5) 175.8 mg (0.180 mmol) of 9-O-propyl-3-O-propionyl-9-dihydrodesmycosin-20-dipropylacetal prepared in (4) was dissolved in a mixed solution of 2.7 ml of acetonitrile and 1.8 ml of water. To this was added 0.028 ml (0.36 mmol) of trifluoro acetic acid and the mixture was stirred for 30 minutes at room temperature. After confirming the completion of the reaction by a thin layer chromatography, the reaction mixture was alkalinized using 5 ml of 7% aqueous ammonia and extracted three times with 30 ml of chloroform. The extract was washed three times with 150 ml of 7% aqueous ammonia and 150 ml of saturated brine, passed through a Watman 1 PS filter, and concentrated under reduced pressure. The residue thus produced was purified by a column chromatography on a silica gel (Art 9385, manufactured by Merck Co.) weighing 4 g, eluting with a gradient of chloroform and chloroform-methanol-concentrated aqueous ammonia (40:1:0.1) to collect the target fractions, thus producing 179.5 mg (0.184 mmol) of 9-O-propyl-3-O-propionyl-9-dihydrodesmycosin at a 102.3% yield.

NMR (CDCl₃) δ ppm 1.75(s, 3H), 2.49(s, 6H), 3.46(s, 3H), 3.60(s, 3H), 4.23(d, 1H, 7 Hz), 4.55(d, 1H, 8 Hz), 4.82–4.86(m, 1H), 5.21(d, 1H, 9 Hz), 5.48(d. d, 1H, 8 Hz, 16 Hz), 6.53(d, 1H, 16 Hz), 9.70(s, 1H)

PREPARATION EXAMPLE 12

Preparation of 9-dihydro-9-O-methyl-3-O-acetyldesmycosin [in formula (I), R¹=acetyl group, R²=methyl group, R³=hydroxyl group, X=—O— mycinose]

(1) 1.22 g (1.42 mmol) of 3-O-acetyldesmycosin-20-dimethylacetal was dissolved in 6 ml of methanol, followed by cooling to 0° C. 161 mg (4.26 mmol) of sodium borohydride was added to the solution and the mixture was stirred for 1 hour at 0° C., and 50 ml of chloroform was added to the reaction mixture. The mixture was washed twice with 20 ml of saturated brine, passed through a Watman 1 PS filter, and concentrated under reduced pressure. The residue thus produced was purified by a column chromatography on a silica gel weighing 20 g, eluting with a gradient of chloroform-methanol (50:1–25:1–15:1) to collect the target fractions, thus producing 997 mg (1.16 mmol) of 9-dihydro-3-O-acetyldesmycosin-20-dimethylacetal at a 81.5% yield.

FAB-Mass: (MH+) 862

NMR (CDCl₃) δ ppm 1.76(s, 3H), 2.10(s, 3H), 2.52(s, 6H), 3.29(s, 3H), 3.34(s, 3H), 3.46(s, 3H), 3.60(s, 3H), 4.24(d, (1H, 7 Hz), 4.52(d, 1H, 8 Hz), 4.6–5.0(m, 1H), 5.40(d, 1H, 10 Hz), 5.46(d. d, 1H, 8 Hz, 16 Hz), 6.36(d, 1H, 16 Hz)

(2) 997 mg (1.16 mmol) of 9-dihydro-3-O-acetyldesmycosin-20-dimethylacetal prepared in (1) was dissolved in 5 ml of methanol, and 107 μl of trifluoro acetic acid was added to the solution and the mixture was stirred for 2 days at room temperature. After the reaction mixture was alkalinized by adding 20 ml of 7% aqueous ammonia, it was extracted three times with 20 ml of chloroform. The chloroform layer collected was washed twice with 50 ml of saturated brine, passed through a Watman 1 PS filter, and concentrated under reduced pressure. The residue thus produced was purified by a column chromatography on a silica gel weighing 20 g, eluting with a gradient of chloroform-methanol (50:1–30:1–20:1) to collect the target fractions, thus producing 384.2 mg (0.44 mmol) of 9-dihydro-9-O-methyl-3-O-acetyldesmycosin-20-dimethylacetal at a 37.8% yield.

FAB-Mass: (MH+) 876

NMR (CDCl₃) δ ppm 1.78(s, 3H), 2.10(s, 3H), 2.50(s, 6H), 3.22(s, 3H), 3.29(s, 3H), 3.35(s, 3H), 3.45(s, 3H), 3.58(s, 3H), 4.24(d, 1H, 7 Hz), 4.50(d, 1H, 8 Hz), 4.6–5.0(m, 1H), 5.12(d, 1H, 10 Hz), 5.40(d, 1H, 10 Hz), 5.46(d. d, 1H, 8 Hz, 16 Hz), 6.36(d, 1H, 16 Hz)

(3) 384.2 mg (0.44 mmol) of 9-dihydro-9-O-methyl-3-O-acetyldesmycosin-20-dimethylacetal prepared in (2) was dissolved in 9.7 ml of a mixed solvent of acetonitrile-water-trifluoro acetic acid (15:10:0.5) and the mixture was stirred for 1 hour at room temperature. The reaction mixture was alkalinized using 30 ml of 7% aqueous ammonia and extracted three times with 30 ml of chloroform. The chloroform layer was washed three times with 50 ml of saturated brine, passed through a Watman 1 PS filter, and concentrated under reduced pressure. The residue thus produced was purified by a column chromatography on a silica gel weighing 10 g, eluting with a gradient of chloroform-methanol (100:1–50:1–30:1–20:1) to produce 202.5 mg (0.24 mmol) of 9-dihydro-9-O-methyl-3-O-acetyldesmycosin at a 55.4% yield.

FAB-Mass: (MH+) 830

NMR (CDCl₃) δ ppm 1.77(s, 3H), 2.23(s, 3H), 2.52(s, 6H), 3.20(s, 3H), 3.44(s, 3H), 3.59(s, 3H), 4.20(d, 1H, 7 Hz), 4.52(d, 1H, 8 Hz), 4.6–5.0(m, 1H), 5.28(d, 1H, 10 Hz), 5.36(d. d, 1H, 8 Hz, 16 Hz), 5.43(d, 1H, 10 Hz), 6.58(d, 1H, 16 Hz), 9.67(s, 1H)

PREPARATION EXAMPLE 13

Preparation of 9-dihydro-9-O-methyl-3-O-acetyl-4'-deoxydesmycosin [in formula (I), R¹=acetyl group, R²=methyl group, R³=hydrogen atom, X=—O— mycinose]

(1) 1.0 g of 3-O-acetyl-4'-deoxydesmycosin was dissolved in 10 ml of methanol. To the solution was added 287 mg of p-toluene sulfonate.1H₂O and the mixture was reacted for 1 hour at room temperature while stirring. The reaction mixture was charged into 100 ml of ice-water and the pH of the mixture was adjusted to 9–10 by adding 7% aqueous ammonia. The mixture was extracted twice with 50 ml of chloroform. The chloroform layer collected was washed with saturated brine, passed through a Watman 1 PS filter, and dried under reduced pressure to obtain a crude material of 3-O-acetyl-4'-deoxydesmycosin-20-dimethylacetal. (2) The crude material of 3-O-acetyl-4'-deoxydesmycosin-20-dimethylacetal prepared in (1) without purification was dissolved in 10 ml of methanol. 190 mg of sodium borohydride was added to the solution and the mixture was reacted for 30 minutes at room temperature while stirring. After the reaction was completed, the reaction mixture was charged into 100 ml of water and extracted twice with 50 ml of chloroform. The chloroform layer collected was washed with twice with 50 ml of saturated brine, passed through a Watman 1 PS filter, and dried under reduced pressure to produce 3-O-acetyl-9-dihydro-4'-deoxydesmycosin-20-dimethylacetal.

(3) The crude 3-O-acetyl-9-dihydro-4'-deoxydesmycosin-20-dimethylacetal prepared in (2) was dissolved in 10 ml of methanol. To the solution was added 1 ml of trifluoro acetic acid and the mixture was reacted for 72 hours at room temperature while stirring. The reaction mixture was charged into 100 ml of ice-water, alkalinized using 7% aqueous ammonia and extracted twice with 50 ml of chloroform. The chloroform layer collected was washed with saturated brine, passed through a Watman 1 PS filter, and dried under reduced pressure to obtain 1.0 g of 3-O-acetyl-9-dihydro-9-O-methyl-4'-deoxydesmycosin-20-dimethylacetal.

(4) 1.0 g of 3-O-acetyl-9-dihydro-9-O-methyl-4'-deoxydesmycosin-20-dimethylacetal prepared in (3) was dissolved in 25 ml of a mixed solvent of acetonitrile-water (3:2 by volume). To the solution was added 1 ml of trifluoro acetic acid and the mixture was reacted for 1.5 hour at room temperature while stirring. The reaction mixture was charged into 100 ml of ice-water, alkalinized using 7% aqueous ammonia and extracted two times with 50 ml of chloroform. The chloroform layer collected was washed with saturated brine and passed through a Watman 1 PS filter. The residue was dried under reduced pressure and purified by column chromatography using 30 g of silica gel (Art 9385; manufactured by Merck Co.), eluting with a gradient of chloroform-methanol-concentrated aqueous ammonia (50:1:0.1–30:1:0.1), thus producing 195 mg of 3-O-acetyl-9-dihydro-9-O-methyl-4'-deoxydesmycosin.

FAB-Mass: 814(MH+) 158
UV$\nu_{max}^{EtOH}$ 236 nm
NMR (CDCl$_3$) δ ppm 1.76(s, 3H), 2.23(s, 3H), 2.27(s, 6H, 3-OAc), 3.19(s, 3H, 9-OMe), 3.45(s, 3H), 3.59(s, 3H), 4.19(d, 1H), 4.55(d, 1H), 4.82(d, t, 1H), 5.22(d, 1H), 5.41(d, 1H), 5.48(d. d, 1H), 6.66(d, 1H), 9.71(s, 1H).

PREPARATION EXAMPLE 14

Preparation of
9-dihydro-9-O-cyclopropylmethyldesmycosin [in formula (I), R$^1$=hydrogen atom, R$^2$=cyclopropylmethyl group, R$^3$=hydroxyl group, X=—O— mycinose]

(1) 430 mg (0.55 mmol) of 9,20-tetrahydrodesmycosin was dissolved in 3 ml of cyclopropane methanol, and 0.6 ml of trifluoro acetic acid was added to the solution and the mixture was stirred over night at 60° C. The reaction mixture was alkalinized using 50 ml of 7% aqueous ammonia and extracted three times with 50 ml of chloroform. The extract was washed three times with 50 ml of 7% aqueous ammonia and 50 ml of saturated brine. The organic layer was passed through a Watman 1 PS filter and concentrated under reduced pressure. The residue was purified by column chromatography using 10 g of silica gel, eluting with a gradient of chloroform-methanol (50:1-30:1-20:1) to produce 280.4 mg (0.34 mmol) of 9-O-cyclopropylmethyl-9,20-tetrahydrodesmycosin (yield: 61.4%).

FAB-Mass: (MH+) 830
NMR (CDCl$_3$) δ ppm; 0.08-0.28(m, 2H), 0.4-0.6(m, 2H), 1.72(s, 3H), 2.50(s, 6H), 3.49(s, 3H), 3.62(s, 3H), 4.30(d, 1H, J=7 Hz), 4.54(d, 1H, J=8 Hz), 4.8-5.1(m, 1H), 5.30(d, 1H, J=10 Hz), 5.62(dd, 1H, J=8 Hz, J=16 Hz), 6.08(d, 1H, J=16 Hz)

(2) 280 mg (0.34 mmol) of 9-O-cyclopropylmethyl-9,20-tetrahydrodesmycosin prepared in (1) was dissolved in 2 ml of methylene chloride, and 160 μl (1.70 mmol) of acetic anhydride was added to the solution and the mixture was stirred for 1 hour at room temperature. The reaction mixture was alkalinized by adding 10 ml of 7% aqueous ammonia and extracted three times with 50 ml of chloroform. The extract was washed three times with 50 ml of 7% aqueous ammonia and 50 ml of saturated brine. The organic layer was passed through a Watman 1 PS filter and concentrated under reduced pressure to produce 262.9 mg (0.29 mmol) of 2',4'-di-O-acetyl-9-O-cyclopropylmethyl-9,20-tetrahydrodesmycosin (yield: 84.6%).

FAB-Mass: (MH+) 914
NMR (CDCl$_3$) δ ppm; 0.08-0.28(m, 2H), 0.4-0.6(m, 2H), 1.71(s, 3H), 2.02(s, 3H), 2.05(s, 3H), 2.33(s, 6H), 3.48(s, 3H), 3.61(s, 3H), 4.52(d, 1H, J=7 Hz), 4.74(d, 1H, J=8 Hz), 5.30(d, 1H, J=10 Hz), 5.60(dd, 1H, J=8 Hz, J=16 Hz), 6.14(d, 1H, J=16 Hz)

(3) 262.9 mg (0.29 mmol) of 2',4'-di-O-acetyl-9-O-cyclopropylmethyl-9,20-tetrahydrodesmycosin prepared in (2) was dissolved in 3 ml of dimethylsulfurtrioxide (hereinafter abbreviated as DMSO). To the solution were added 224 μl (1.62 mmol) of triethylamine and 91.5 mg (0.58 mmol) of pyridinesulfurtrioxide and the mixture was stirred for 1 hour at room temperature. The reaction mixture was added to 100 ml of water containing 5% of 7% aqueous ammonia and 5% of saturated brine. The precipitate produced was collected by filtration and dissolved in 50 ml of chloroform. The mixture was washed three times with 50 ml of 7% aqueous ammonia and 50 ml of saturated brine. The chloroform layer was passed through a Watman 1 PS filter and concentrated under reduced pressure. The residue was purified by a column chromatography on a silica gel weighing 10 g, eluting with a gradient of toluene-acetone (50:1-20:1-15:1-10:1-7:1-5:1) to produce 91.2 mg (0.10 mmol) of 9-dihydro-2',4'-di-O-acetyl-9-O-cyclopropylmethyldesmycosin (yield: 34.5%).

FAB-Mass: (MH+) 912
NMR (CDCl$_3$) δ ppm; 0.06-0.22(m, 2H), 0.4-0.6(m, 2H), 1.71(s, 3H), 2.02(s, 3H), 2.05(s, 3H), 2.33(s, 6H), 3.48(s, 3H), 3.61(s, 3H), 4.52(d, 1H, J=7 Hz), 4.74(d, 1H, J=8 Hz), 5.32(d, 1H, J=10 Hz), 5.56(dd, 1H, J=8 Hz, J=16 Hz), 6.16(d, 1H, J=16 Hz)

(4) 91.2 mg (0.10 mmol) of 9-dihydro-2',4'-di-O-acetyl-9-O-cyclopropylmethyldesmycosin prepared in (3) was dissolved in 10 ml of methanol and the mixture was stirred over night at 65° C. The solution was concentrated under reduced pressure. The residue was dissolved in 50 ml of chloroform. The mixture was washed three times with 50 ml of 7% aqueous ammonia and 50 ml of saturated brine. The organic layer was passed through a Watman 1 PS filter and concentrated under reduced pressure. The residue was purified by a column chromatography on a silica gel weighing 10 g, eluting with a gradient of chloroform-methanol (50:1-30:1-20:1-10:1) to collect the target fractions. The fractions were further purified by preparative HPLC eluting with 0.05M aqueous NaH$_2$PO$_4$-methanol (35:65) to produce 82.0 mg (0.01 mmol) of 9-dihydro-9-O-cyclopropylmethyldesmycosin (yield: 97.8%).

FAB-Mass: (MH+) 828
NMR (CDCl$_3$) δ ppm; 0.04-0.22(m, 2H), 0.36-0.56(m, 2H), 1.73(s, 3H), 2.49(s, 6H), 3.49(s, 3H), 3.62(s, 3H), 4.30(d, 1H, J=7 Hz), 4.52(d, 1H, J=8 Hz), 4.78-5.08(m, 1H), 5.32(d, 1H, J=10 Hz), 5.54(dd, 1H, J=8 Hz, J=16 Hz), 6.12(d, 1H, J=16 Hz), 9.74(s, 1H)

PREPARATION EXAMPLE 15

Preparation of
9-dihydro-9-O-cyclobutylmethyldesmycosin [in formula (I), R$^1$=hydrogen atom, R$^2$=cyclobutylmethyl group, R$^3$=hydroxyl group, X=—O— mycinose]

(1) 543 mg (0.70 mmol) of 9,20-tetrahydrodesmycosin was dissolved in 4.5 ml of cyclobutyl methanol, and 1.0 ml of trifluoro acetic acid was added to the solution and the mixture was stirred for 5 hours at 70° C., followed by stirring at room temperature over night. The reaction mixture was alkalinized using 50 ml of 7% aqueous ammonia and extracted three times with 50 ml of chloroform. The extract was washed twice with 50 ml of 7% aqueous ammonia and 50 ml of saturated brine. The organic layer was passed through a Watman 1 PS filter and concentrated under reduced pressure. The residue was purified by column chromatography using 10 g of silica gel, eluting with a gradient of chloroform-methanol (50:1-30:1-20:1) to produce 286.1 mg (0.34 mmol) of 9-O-cyclobutylmethyl-9,20-tetrahydrodesmycosin (yield: 48.4%).

FAB-Mass: (MH+) 844
NMR (CDCl$_3$) δ ppm; 1.74(s, 3H), 2.49(s, 6H), 3.50(s, 3H), 3.61(s, 3H), 4.28(d, 1H, J=7 Hz), 4.53(d, 1H, J=8 Hz), 4.8-5.1(m, 1H), 5.30(d, 1H, J=10 Hz), 5.60(dd, 1H, J=8 Hz, J=16 Hz), 6.10(d, 1H, J=16 Hz)

(2) 286.1 mg (0.34 mmol) of 9-O-cyclobutylmethyl-9,20-tetrahydrodesmycosin prepared in (1) was dissolved in 2 ml of methylene chloride, and 160 μl (1.70 mmol) of acetic anhydride was added to the solution and the mixture was stirred for 1 hour at room temperature. The reaction mixture was alkalinized by adding 10 ml of 7% aqueous ammonia and extracted three times with 50 ml of chloroform. The extract was washed three times with 50 ml of 7% aqueous ammonia and 50 ml of saturated brine. The organic layer was passed through a Watman 1 PS filter and concentrated under reduced pressure to produce 298.2 mg (0.32 mmol) of 2',4'-di-O-acetyl-9-O-cyclobutylmethyl-9,20-tetrahydrodesmycosin (yield: 94.1%).

FAB-Mass: (MH+) 928

NMR (CDCl$_3$) δ ppm; 1.72(s, 3H), 2.04(s, 3H), 2.06(s, 3H), 2.35(s, 6H), 3.48(s, 3H), 3.61(s, 3H), 4.52(d, 1H, J=7 Hz), 4.73(d, 1H, J=8 Hz), 5.30(d, 1H, J=10 Hz), 5.60(dd, 1H, J=8 Hz, J=16 Hz), 6.14(d, 1H, J=16 Hz).

(3) 298.2 mg (0.32 mmol) of 2',4'-di-O-acetyl-9-O-cyclobutylmethyl-9,20-tetrahydrodesmycosin prepared in (2) was dissolved in 3 ml of DMSO. To the solution were added 250 μl (1.79 mmol) of triethylamine and 102.2 mg (0.64 mmol) of pyridinesulfurtrioxide and the mixture was stirred for 1 hour at room temperature. Since the unreacted raw material was confirmed by a thin layer chromatography, 51.1 mg (0.32 mmol) of pyridinesulfurtrioxide was further added and the reaction was continued for 1 hour at room temperature with stirring. The reaction solution was added to 100 ml of water containing 7% aqueous ammonia (5%) and saturated brine (5%). The precipitate thus obtained was collected by filtration, dissolved in 50 ml of chloroform, and washed three times with 50 ml of 7% aqueous ammonia and 50 ml of saturated brine. The organic layer was passed through a Watman 1 PS filter and concentrated under reduced pressure. The residue was purified by a column chromatography on a silica gel weighing 10 g, eluting with a gradient of toluene-acetone (50:1-20:1-10:1) to produce 107.1 mg (0.12 mmol) of 9-dihydro-2',4'-di-O-acetyl-9-O-cyclobutylmethyldesmycosin (yield: 36.0%).

FAB-Mass: (MH+) 926

NMR (CDCl$_3$) δ ppm; 1.72(s, 3H), 2.03(s, 3H), 2.06(s, 3H), 2.33(s, 6H), 3.49(s, 3H), 3.61(s, 3H), 4.52(d, 1H, J=7 Hz), 4.72(d, 1H, J=8 Hz), 5.32(d, 1H, J=10 Hz), 5.44(dd, 1H, J=8 Hz, J=16 Hz), 6.16(d, 1H, J=16 Hz), 9.76(s, 1H)

(4) 107.1 mg (0.12 mmol) of 9-dihydro-2',4'-di-O-acetyl-9-O-cyclobutylmethyldesmycosin prepared in (3) was dissolved in 10 ml of methanol and the mixture was stirred over night at 55° C. The solution was concentrated under reduced pressure. The residue was dissolved in 50 ml of chloroform. The mixture was washed three times with 50 ml of 7% aqueous ammonia and 50 ml of saturated brine. The organic layer was passed through a Watman 1 PS filter and concentrated under reduced pressure. The residue was purified by preparative HPLC eluting with 0.05M aqueous NaH$_2$PO$_4$-methanol (35:65) to produce 33.1 mg (0.04 mmol) of 9-dihydro-9-O-cyclobutylmethyldesmycosin (yield: 32.6%).

FAB-Mass: (MH+) 842

NMR (CDCl$_3$) δ ppm; 1.73(s, 3H), 2.49(s, 6H), 3.49(s, 3H), 3.61(s, 3H), 4.29(d, 1H, J=7 Hz), 4.51(d, 1H, J=8 Hz), 4.8-5.1(m, 1H), 5.32(d, 1H, J=10 Hz], 5.52(dd, 1H, J=8 Hz, J=16 Hz), 6.12(d, 1H, J=16 Hz), 9.73(s, 1H)

PREPARATION EXAMPLE 16

Preparation of 9-dihydro-9-O-cyclohexylmethyldesmycosin [in formula (I), $R^1$=hydrogen atom, $R^2$=cyclohexylmethyl group, $R^3$=hydroxyl group, X=—O— mycinose]

(1) 543 mg (0.70 mmol) of 9,20-tetrahydrodesmycosin was dissolved in 4.5 ml of cyclohexyl methanol, and 1.0 ml of trifluoro acetic acid was added to the solution and the mixture was stirred for 5 hours at 70° C., followed by stirring at room temperature over night. The reaction mixture was alkalinized using 50 ml of 7% aqueous ammonia and extracted three times with 50 ml of chloroform. The extract was washed twice with 50 ml of 7% aqueous ammonia and 50 ml of saturated brine. The organic layer was passed through a Watman 1 PS filter and concentrated under reduced pressure. The residue was purified by column chromatography using 10 g of silica gel, eluting with a gradient of chloroform-methanol (50:1-30:1-20:1) to produce 361.4 mg (0.41 mmol) of 9-O-cyclohexylmethyl-9,20-tetrahydrodesmycosin (yield: 59.2%).

FAB-Mass (MH+) 872

NMR (CDCl$_3$) δ ppm; 1.74(s, 3H), 2.49(s, 6H), 3.50(s, 3H), 3.62(s, 3H), 4.30(d, 1H, J=7 Hz), 4.54(d, 1H, J=8 Hz), 4.8-5.1(m, 1H), 5.32(d, 1H, J=10 Hz), 5.62(dd, 1H, J=8 Hz, J=16 Hz), 6.10(d, 1H, J=16 Hz)

(2) 361.4 mg (0.41 mmol) of 9-O-cyclohexylmethyl-9,20-tetrahydrodesmycosin prepared in (1) was dissolved in 2 ml of methylene chloride, and 160 μl (1.70 mmol) of acetic anhydride was added to the solution and the mixture was stirred for 1 hour at room temperature. The reaction mixture was alkalinized by adding 10 ml of 7% aqueous ammonia and extracted three times with 50 ml of chloroform. The extract was washed three times with 50 ml of 7% aqueous ammonia and 50 ml of saturated brine. The organic layer was passed through a Watman 1 PS filter and concentrated under reduced pressure to produce 400.4 mg (0.42 mmol) of 2',4'-di-O-acetyl-9-O-cyclohexylmethyl-9,20-tetrahydrodesmycosin (yield: 101.0%).

FAB-Mass: (MH+) 956

NMR (CDCl$_3$) δ ppm; 1.72(s, 3H), 2.03(s, 3H), 2.06(s, 3H), 2.33(s, 6H), 3.48(s, 3H), 3.60(s, 3H), 4.52(d, 1H, J=7 Hz), 4.74(d, 1H, J=8 Hz), 5.30(d, 1H, J=10 Hz), 5.50(dd, 1H, J=8 Hz, 16 Hz), 6.12(d, 1H, J=16 Hz).

(3) 400.4 mg (0.42 mmol) of 2',4'-di-O-acetyl-9-O-cyclohexylmethyl-9,20-tetrahydrodesmycosin prepared in (2) was dissolved in 3.6 ml of DMSO. To the solution were added 305 μl (2.19 mmol) of triethylamine and 124.3 mg (0.78 mmol) of pyridinesulfurtrioxide and the mixture was stirred for 1 hour at room temperature. Since the unreacted raw material was confirmed by a thin layer chromatography, 62.2 mg (0.39 mmol) of pyridinesulfurtrioxide was further added and the reaction was continued with stirring for 1 hour at room temperature. The reaction solution was added to 100 ml of water containing 7% aqueous ammonia (5%) and saturated brine (5%). The precipitate thus obtained was collected by filtration, dissolved in 50 ml of chloroform, and washed three times with 50 ml of 7% aqueous ammonia and 50 ml of saturated brine. The organic layer was passed through a Watman 1 PS filter and concentrated under reduced pressure. The residue was purified by a column chromatography on a silica gel weighing 10 g, eluting with a gradient of toluene-acetone (50:1-20:1-10:1) to produce 111.3 mg (0.12 mmol) of 9-dihydro-2',4'-di-O-acetyl-9-O-cyclohexylmethyldesmycosin (yield: 27.8%).

FAB-Mass: (MH+) 954

NMR (CDCl$_3$) δ ppm; 1.71(s, 3H), 2.02(s, 3H), 2.05(s, 3H), 2.34(s, 6 Hz), 3.49(s, 3H), 3.61(s, 3H), 4.52(d, 1H, J=7 Hz), 4.74(d, 1H, J=8 Hz), 5.34(d, 1H, J=10 Hz), 5.44(dd, 1H, J=8 Hz, J=16 Hz), 6.16(d, 1H, J=16 Hz), 9.76(s, 1H), (4) 111.3 mg (0.12 mmol) of 9-dihydro-2',4'-di-O-acetyl-9-O-cyclohexylmethyldesmycosin prepared in (3) was dissolved in 10 ml of methanol and the mixture was stirred over night at 55° C. The solution was concentrated under reduced pressure. The residue was dissolved in 50 ml of chloroform. The mixture was washed three times with 50 ml of 7% aqueous ammonia and 50 ml of saturated brine. The organic layer was passed through a Watman 1 PS filter and concentrated under reduced pressure. The residue was purified by preparative HPLC eluting with 0.05M aqueous NaH$_2$PO$_4$-methanol (35:65) to produce 20.8 mg (0.02 mmol) of 9-dihydro-9-O-cyclohexylmethyldesmycosin (yield: 19.9%).

FAB-Mass: (MH+) 870

NMR (CDCl$_3$) δ ppm; 1.73(s, 3H), 2.50(s, 6H), 3.49(s, 3H), 3.62(s, 3H), 4.29(d, 1H, J=7 Hz), 4.52(d, 1H, J=8 Hz), 4.8-5.1(m, 1H), 5.31(d, 1H, J=10 Hz), 5.53(dd, 1H, J=8 Hz, J=16 Hz), 6.12(d, 1H, J=16 Hz), 9.73(s, 1H)

PREPARATION EXAMPLE 17

Preparation of 9-dihydro-9-O-isobutyldesmycosin [in formula (I), R$^1$=hydrogen atom, R$^2$=isobutyl group, R$^3$=hydroxyl group, X=—O— mycinose]

(1) 543 mg (0.70 mmol) of 9,20-tetrahydrodesmycosin was dissolved in 5 ml of isobutanol. 1.0 ml of trifluoro acetic acid was added to the solution and the mixture was stirred for 7 hours at 70° C. The reaction mixture was added to 100 ml of water containing 7% aqueous ammonia (5%) and saturated brine (5%). The precipitate thus produced was collected by filtration and dissolved in 50 ml of chloroform. The mixture was washed twice with 50 ml of 7% aqueous ammonia and 50 ml of saturated brine. The organic layer was passed through a Watman 1 PS filter and concentrated under reduced pressure. The residue was purified by column chromatography using 10 g of silica gel, eluting with a gradient of chloroform-methanol (30:1-20:1-15:1-10:1) to produce 210 mg (0.25 mmol) of 9-O-isobutyl-9,20-tetrahydrodesmycosin (yield: 36.0%).

FAB-Mass: (MH+) 832

NMR (CDCl$_3$) δ ppm; 1.72(s, 3H), 2.50(s, 6H), 3.49(s, 3H), 3.62(s, 3H), 4.30(d, 1H, J=7 Hz), 4.54(d, 1H, J=8 Hz), 4.8-5.1(m, 1H), 5.30(d, 1H, J=10 Hz), 5.62(dd, 1H, J=8 Hz, J=16 Hz), 6.08(d, 1H, J=16 Hz).

(2) 210 mg (0.25 mmol) of 9-O-isobutyl-9,20-tetrahydrodesmycosin prepared in (1) was dissolved in 2 ml of chloroform. 120 μl (1.28 mmol) of acetic anhydride was added to the solution and the mixture was stirred for 1 hour at room temperature. The reaction mixture was alkalinized by adding 10 ml of 7% aqueous ammonia and extracted three times with 50 ml of chloroform. The extract was washed three times with 50 ml of 7% aqueous ammonia and 50 ml of saturated brine. The organic layer was passed through a Watman 1 PS filter and concentrated under reduced pressure to produce 231.7 mg (0.25 mmol) of 2',4'-di-O-acetyl-9-O-isobutyl-9,20-tetrahydrodesmycosin (yield: 100%).

FAB-Mass: (MH+) 916

NMR (CDCl$_3$) δ ppm; 1.71(s, 3H), 2.03(s, 3H), 2.05(s, 3H), 2.33(s, 6H), 3.48(s, 3H), 3.61(s, 3H), 4.55(d, 1H, J=7 Hz), 4.78(d, 1H, J=8 Hz), 5.33(d, 1H, J=10 Hz), 5.62(dd, 1H, J=8 Hz, J=16 Hz), 6.18(d, 1H, J=16 Hz).

(3) 231.7 mg (0.25 mmol) of 2',4'-di-O-acetyl-9-O-isobutyl-9,20-tetrahydrodesmycosin prepared in (2) was dissolved in 3 ml of DMSO. To the solution were added 239 μl (1.71 mmol) of triethylamine and 97.1 mg (0.61 mmol) of pyridinesulfurtrioxide and the mixture was stirred for 1 hour at room temperature. The reaction solution was added to 100 ml of water containing 7% aqueous ammonia (5%) and saturated brine (5%). The precipitate thus obtained was collected by filtration, dissolved in 50 ml of chloroform, and washed three times with 50 ml of 7% aqueous ammonia and 50 ml of saturated brine. The organic layer was passed through a Watman 1 PS filter and concentrated under reduced pressure. The residue was purified by a column chromatography on a silica gel weighing 10 g, eluting with a L gradient of chloroform-methanol (200:1-150:1-100-:1-50:1) to produce 81.5 mg (0.09 mmol) of 9-dihydro-2',4'-di-O-acetyl-9-O-isobutyldesmycosin (yield: 35.6%) with the existence of 91.6 mg (0.1 mmol) of the raw material (yield: 40.0%).

FAB-Mass: (MH+) 914

NMR (CDCl$_3$) δ ppm; 1.72(s, 3H), 2.02(s, 3H), 2.05(s, 3H), 2.33(s, 6H), 3.48(s, 3H), 3.61(s, 3H), 4.51(d, 1H, J=7 Hz), 4.74(d, 1H, J=8 Hz), 5.32(d, 1H, J=10 Hz), 5.44(dd, 1H, J=8 Hz, J=16 Hz), 6.16(d, 1H, J=16 Hz), 9.76(s, 1H)

(4) 81.5 mg (0.09 mmol) of 9-dihydro-2',4'-di-O-acetyl-9-O-isobutyldesmycosin prepared in (3) was dissolved in 5 ml of methanol and the mixture was stirred over night at 55° C. The solution was concentrated under reduced pressure. The residue was dissolved in 50 ml of chloroform. The mixture was washed three times with 50 ml of 7% aqueous ammonia and 50 ml of saturated brine. The organic layer was passed through a Watman 1-PS filter and concentrated under reduced pressure. The residue was purified by preparative HPLC eluting with 0.05M aqueous NaH$_2$PO$_4$-methanol (35:65) to produce 28.7 mg (0.03 mmol) of 9-dihydro-9-O-isobutyldesmycosin (yield: 38.3%).

FAB-Mass: (MH+) 830

NMR (CDCl$_3$) δ ppm; 1.72(s, 3H), 2.49(s, 6H), 3.49(s, 3H), 3.61(s, 3H), 4.29(d, 1H, J=7 Hz), 4.52(d, 1H, J=8 Hz), 4.8-5.1 (m, 1H), 5.32(d, 2H, J=10 Hz), 5.54(dd, 1H, J=8 Hz, J=16 Hz), 6.12(d, 1H, J=16 Hz), 9.73(s, 1H).

PREPARATION EXAMPLE 18

Preparation of 9-dihydro-9-O-benzyldesmycosin [in formula (I), R$^1$=hydrogen atom, R$^2$=benzyl group, R$^3$=hydroxyl group, X=—O— mycinose]

(1) 543 mg (0.70 mmol) of 9,20-tetrahydrodesmycosin was dissolved in 3 ml of benzyl alcohol, 0.6 ml of trifluoro acetic acid was added to the solution and the mixture was stirred for 6 hours at 70° C. The reaction solution was added to 150 ml of water containing 7% aqueous ammonia (5%) and saturated brine (5%). The precipitate thus produced was collected by filtration and dissolved in 50 ml of chloroform. The mixture was washed twice with 50 ml of 7% aqueous ammonia and 50 ml of saturated brine. The organic layer was passed through a Watman 1 PS filter and concentrated under reduced pressure. The residue was purified by column chromatography using 10 g of silica gel, eluting with a gradient of chloroform-methanol (30:1-20:1-15:1-10:1) to produce 360.6 mg (0.42 mmol) of 9-O-benzyl-9,20-tetrahydrodesmycosin (yield: 59.5%).

FAB-Mass: (MH+) 866

NMR (CDCl$_3$) δ ppm; 1.74(s, 3H), 2.48(s, 6H), 3.51(s, 3H), 3.62(s, 3H), 4.30(d, 1H, J=7 Hz), 4.56(d, 1H, J=8 Hz), 4.8–5.1(m, 1H), 5.34(d, 1H, J=10 Hz), 5.68(dd, 1H, J=8 Hz, J=16 Hz), 6.12(d, 1H, J=16 Hz)

(2) 360.6 mg (0.42 mmol) of 9-O-benzyl-9,20-tetrahydrodesmycosin prepared in (1) was dissolved in 3 ml of chloroform, and 196 μl (2.10 mmol) of acetic anhydride was added to the solution and the mixture was stirred for 1 hour at room temperature. The reaction mixture was alkalinized by adding 10 ml of 7% aqueous ammonia and extracted three times with 50 ml of chloroform. The extract was washed three times with 50 ml of 7% aqueous ammonia and 50 ml of saturated brine. The organic layer was passed through a Watman 1 PS filter and concentrated under reduced pressure to produce 468.2 mg of 2′,4′-di-O-acetyl-9-O-benzyl-9,20-tetrahydrodesmycosin.

FAB-Mass: (MH+) 950

NMR (CDCl$_3$) δ ppm, 1.73(s, 3H), 2.02(s, 3H), 2.04(s, 3H), 2.33(s, 6H), 3.50(s, 3H), 3.61(s, 3H), 4.56(d, 1H, J=7 Hz), 4.77(d, 1H, J=8 Hz), 5.36(d, 1H, J=10 Hz), 5.60(dd, 1H, J=8 Hz, J=16 Hz), 6.18(d, 1H, J=16 Hz)

(3) 468.2 mg of 2′,4′-di-O-acetyl-9-O-benzyl-9,20-tetrahydrodesmycosin prepared in (2) was dissolved in 3 ml of DMSO. To the solution were added 577 μl (4.14 mmol) of triethylamine and 235 mg (1.47 mmol) of pyridinesulfurtrioxide and the mixture was stirred for 1 hour at room temperature. The reaction solution was added to 100 ml of water containing 7% aqueous ammonia (5%) and saturated brine (5%). The precipitate thus obtained was collected by filtration, dissolved in 50 ml of chloroform, and washed three times with 50 ml of 7% aqueous ammonia and 50 ml of saturated brine. The organic layer was passed through a Watman 1 PS filter and concentrated under reduced pressure. The residue was purified by a column chromatography on a silica gel weighing 10 g, eluting with a gradient of chloroform-methanol (200:1-150:1-100:1-75:1) to produce 192.7 mg (0.20 mmol) of 9-dihydro-2′,4′-di-O-acetyl-9-O-benzyldesmycosin (yield: 41.5%).

FAB-Mass: (MH+) 948

NMR (CDCl$_3$) δ ppm; 1.74(s, 3H), 2.02(s, 3H), 2.04(s, 3H), 2.33(s, 6H), 3.50(s, 3H), 3.61(s, 3H), 4.52(d, 1H, J=7 Hz), 4.72(d, 1H, J=8 Hz), 5.34(d, 1H, J=10 Hz), 5.52(dd, 1H, J=8 Hz, J=16 Hz), 6.20(d, 1H, J=16 Hz), 9.65(s, 1H)

(4) 192.7 mg (0.20 mmol) of 9-dihydro-2′,4′-di-O-acetyl-9-O-benzyldesmycosin prepared in (3) was dissolved in 5 ml of methanol and the mixture was stirred over night at 55° C. The solution was concentrated under reduced pressure. The residue was dissolved in 50 ml of chloroform. The mixture was washed three times with 50 ml of 7% aqueous ammonia and 50 ml of saturated brine. The organic layer was passed through a Watman 1 PS filter and concentrated under reduced pressure. The residue was purified by preparative HPLC eluting with 0.05M aqueous NaH$_2$PO$_4$-methanol (35:65) to produce 70.4 mg (0.08 mmol) of 9-dihydro-9-O-benzyldesmycosin (yield: 40.7%).

FAB-Mass: (MH+) 864

NMR (CDCl$_3$) δ ppm; 1.74(s, 3H), 2.48(s, 6H), 3.50(s, 3H), 3.62(s, 3H), 4.28(d, 1H, J=7 Hz), 4.52(d, 1H, J=8 Hz), 4.8–5.1(m, 1H), 5.32(d, 1H, J=10 Hz), 5.58(dd, J=8 Hz, J=16 Hz), 6.14(d, 1H, J=16 Hz), 9.69(s, 1H)

REFERENCE EXAMPLE

Preparation of 9,20-tetrahydrodesmycosin 3.86 g (5.00 mmol) of desmycosin was dissolved in 40 ml of methanol. To the solution was added 0.38 g (10.0 mmol) of sodium borohydride and the mixture was stirred for 1 hour at 0°–5° C. Concentrated hydrochloric acid was slowly added to the reaction mixture to adjust to pH 7. The mixture was alkalinized by adding 50 ml of 7% aqueous ammonia and extracted three times with 50 ml of chloroform. The extract was washed three times with 50 ml of 7% aqueous ammonia and 50 ml of saturated brine. The organic layer was passed through a Watman 1 PS filter and concentrated under reduced pressure to produce 3.87 g (4.99 mmol) of 9,20-tetrahydrodesmycosin (yield: 99.7%). This product, however, was confirmed to be the mixture of 9R and 9S (23.4:76.6). A small amount of the product was subjected to preparative HPLC eluting with 0.05M aqueous NaH$_2$PO$_4$-methanol (35:65) to obtain a 9R isomer and a 9S isomer separately.

9(R)-9,20-tetrahydrodesmycosin

FAB-Mass: (MH+) 776

NMR (CDCl$_3$) δ ppm; 1.72(s, 3H), 2.49(s, 3H), 3.49(s, 3H), 3.61(s, 3H), 4.32(d, 1H, J=7 Hz), 4.55(d, 1H, J=8 Hz), 4.8–5.1(m, 1H), 5.30(d, 1H, J=10 Hz), 5.62(dd, 1h, J=8 Hz, J=16 Hz), 6.60(d, 1H, J=16 Hz)

9(S)-9,20-tetrahydrodesmycosin

FAB-Mass: (MH+) 776

NMR (CDCl$_3$) δ ppm; 1.72(s, 3H), 2.49(s, 3H), 3.50(s, 3H), 3.61(s, 3H), 4.28(d, 1H, J=7 Hz), 4.52(d, 1H, J=8 Hz), 4.8–5.1(m, 1H), 5.36(d, 1H, J=10 Hz), 5.92(dd, 1H, J=4 Hz, J=16 Hz), 6.42(d, 1H, J=16 Hz)

PREPARATION EXAMPLE 19

Preparation of 9-dihydro-9-O-methyldesmycosin (1) 776 mg (1.00 mmol) of 9,20-tetrahydrodesmycosin was dissolved in 5 ml of methanol, and 92.5 μl (1.2 mmol) of trifluoro acetic acid was added to the solution and the mixture was stirred at 40° C. over night. The reaction solution was charged into 20 ml of 7% aqueous ammonia and the mixture was extracted three times with chloroform. The chloroform layer was collected, washed twice with 50 ml of saturated brine, and passed through a Watman 1 PS filter. The filtrate was concentrated under reduced pressure. The residue was purified by column chromatography using 20 g of silica gel (Art 9385 manufactured by Merck Co.), eluting with a gradient of chloroform-methanol (50:1-30:1-20:1) to produce 650.3 mg (0.82 mmol) of 9-O-methyl-9,20-tetrahydrodesmycosin (yield: 82.3%).

(2) 150.3 mg (0.82 mmol) of 9-O-methyl-9,20-tetrahydrodesmycosin prepared in (1) was dissolved in 5 ml of methylene chloride, and 233 μl (2.47 mmol) of acetic anhydride was added to the solution and the mixture was stirred for 1 hour at room temperature. To the reaction mixture was added 20 ml of 7% aqueous ammonia and the mixture was extracted three times with 20 ml of chloroform. The chloroform layer was collected, washed two times with 50 ml of saturated brine, and passed through a Watman 1 PS filter. The filtrate was concentrated under reduced pressure. The residue was purified by column chromatography using 20 g of silica gel (Art 9385, manufactured by Merck Co.), eluting with a gradient of chloroform-methanol (70:1–50:1–30:1) to produce 586.4 mg (0.67 mmol) of 2',4'-di-O-acetyl-9-O-methyl-9,20-tetrahydrodesmycosin (yield: 81.5%).

(3) 586.4 mg (0.67 mmol) of 2',4'-di-O-acetyl-9-O-methyl-9,20-tetrahydrodesmycosin prepared in (2) was dissolved in 6 ml of DMSO. To the solution were added 523 μl (3.75 mmol) of triethylamine and 213 mg (1.34 mmol) of pyridinesulfurtrioxide and the mixture was stirred for 1 hour at room temperature. The reaction solution was added to 200 ml of water containing 7% aqueous ammonia (5%) and saturated brine (5%). The precipitate thus obtained was collected by filtration, dissolved in 50 ml of chloroform, and washed twice with 50 ml of 7% aqueous ammonia and 50 ml of saturated brine. The solution obtained was passed through a Watman 1 PS filter and concentrated under reduced pressure. The residue was purified by a column chromatography on a silica gel weighing 20 g, eluting with a gradient of toluene-acetone (50:1–20:1–10:1–7:1–5:1) to produce 221.1 mg (0.25 mmol) of 9-dihydro-2',4'-di-O-acetyl-9-O-methyldesmycosin (yield: 37.8%).

(4) 221.1 mg (0.25 mmol) of 9-dihydro-2',4'-di-O-acetyl-9-O-methyldesmycosin prepared in (3) was dissolved in 3 ml of methanol and the mixture was stirred over night at 55° C. The reaction solution was concentrated under reduced pressure. The residue was purified by preparative HPLC eluting with 0.05M aqueous NaH$_2$PO$_4$-methanol (35:65) to produce 179.1 mg (0.23 mmol) of 9-dihydro-9-O-methyldesmycosin (yield: 89.7%).

FAB-Mass: (MH+) 788
UV$\nu_{max}^{EtOH}$ 236 nm
NMR(CDCl$_3$) δ ppm: 1.74(s, 3H), 2.50(s, 6H), 3.20(s, 3H, 9-OMe), 3.50(s, 3H), 3.62(s, 3H), 4.32(d, 1H), 4.56(d, 1H), 4.98(d. t, 1H), 5.39(d, 1H), 5.56(d. d, 1H), 6.23(d, 1H), 9.75(s, 1H),

PREPARATION EXAMPLE 20–30

The same procedures as in Preparation Example 19 were performed to produce the following compounds.
Preparation Example 20: 9-dihydro-9-O-ethyldesmycosin
Preparation Example 21: 9-dihydro-9-O-propyldesmycosin
Preparation Example 22: 9-dihydro-9-O-butyldesmycosin
Preparation Example 23: 9-dihydro-9-O-methyl-3-O-propionyldesmycosin
Preparation Example 24: 9-dihydro-9-O-methyl-4'-deoxydesmycosin
Preparation Example 25: 9-dihydro-9-O-ethyl-3-O-acetyldesmycosin
Preparation Example 26: 9-dihydro-9-O-propyl-3-O-acetyldesmycosin
Preparation Example 27: 9-dihydro-9-O-ethyl-3-O-propionyldesmycosin
Preparation Example 28: 9-dihydro-9-O-propyl-3-O-propionyldesmycosin
Preparation Example 29: 9-dihydro-9-O-methyl-3-O-acetyldesmycosin
Preparation Example 30: 9-dihydro-9-O-methyl-3-O-acetyl-4'-deoxydesmycosin Obviously, numerous modifications and variations of the present invention are possible in light of the above teachings. It is therefore to be understood that the scope of the appended claims, the invention may be practiced otherwise than as specifically described herein.

What is claimed is:

1. A 9-dihydro-9-O-alkyldesmycosin derivative represented by the following formula (I),

[Chemical structure of formula (I)]

wherein X represents an —O— mycinose or a di-lower alkylamino group, R$^1$ represents a hydrogen atom or a lower alkanoyl group, R$^2$ represents a lower alkyl group, a C$_3$–C$_6$ cycloalkyl-lower alkyl group, or substituted phenyl-lower alkyl group wherein the substituent is selected from the group consisting of hydrogen, halogen, C$_1$–C$_4$ alkyl and C$_1$–C$_4$ alkoxy, and R$^3$ represents a hydrogen atom or a hydroxyl group; or a salt thereof.

2. A 9-dihydro-9-O-alkyldesmycosin derivative according to claim 1, wherein R$^1$ is selected from the group consisting of hydrogen and C$_2$–C$_4$ alkanoyl, and R$_2$ is selected from the group consisting of C$_1$–C$_4$ alkyl, C$_{3-6}$-cycloalkyl-methyl, benzyl and phenylethyl, or a salt thereof.

3. A 9-dihydro-9-O-alkyldesmycosin derivative or a salt thereof according to claim 1, wherein said derivative is selected from the group consisting of:
9-dihydro-9-O-methyldesmycosin, 9-dihydro-9-O-methyl-4'-deoxydesmycosin, 9-dihydro-9-O-ethyldesmycosin,
9-dihydro-9-O-ethyl-4'-deoxydesmycosin, 9-dihydro-9-O-propyldesmycosin, 9-dihydro-9-O-butyldesmycosin,
9-dihydro-9-O-isobutyldesmycosin, 9-dihydro-9-O-methyl-3-O-acetyldesmycosin, 9-dihydro-9-O-methyl-3-O-propionyldesmycosin, 9-dihydro-9-O-methyl-3-O-acetyl-4'-deoxydesmycosin, 9-dihydro-9-O-methyl-3-O-propionyl-4'-deoxydesmycosin, 9-dihydro-9-O-ethyl-3-O-acetyldesmycosin,
9-dihydro-9-O-ethyl-3-O-propionyldesmycosin, 9-dihydro-9-O-propyl-3-O-acetyldesmycosin, 9-dihydro-9-O-propyl-3-O-propionyldesmycosin, 9-dihydro-9-O-butyl-3-O-acetyldesmycosin,
9-dihydro-9-O-butyl-3Opropionyldesmycosin, 9-dihydro-9-O-isobutyl-3-O-acetyldesmycosin, 9-dihydro-9-O-isobutyl-3-O-propionyldesmycosin, 9-dihydro-9-O-cyclopropylmethyldesmycosin, 9-dihydro-9-O-cyclobutylmethyldesmycosin,
9-dihydro-9-O-cyclopentylmethyldesmycosin, 9-dihydro-9-O-cyclohexylmethyldesmycosin, 9-dihydro-9-O-cyclopropylmethyl-3-O-acetyldesmycosin, 9-dihydro-9-O-cyclopropylmethyl-3-O-propionyldesmycosin, 9-dihydro-9-O-cyclobutylmethyl-3-O-acetyldesmycosin, 9-dihydro-9-O-cyclobutylmethyl-3-O-propionyldesmycosin, 9-dihydro-9-O-cyclopentylmethyl-3-O-acetyldesmycosin, 9-dihydro-9-O-cyclopentylmethyl-3-O-propionyldesmycosin, 9-dihydro-9-O-cyclohexylmethyl-3-O-acetyldesmycosin, 9-dihydro-9-O-cyclohexylmethyl-3-O-propionyldesmycosin, 9-dihydro-9-O-cyclohexylmethyl-4'-deoxydesmycosin, 9-dihydro-9-O-benzyldesmycosin,
9-dihydro-9-O-benzyl-3-O-acetyldesmycosin, 9-dihydro-9-O-benzyl-3-O-propionyldesmycosin, 9-dihydro-9-O-benzyl-4'-deoxydesmycosin and 9-dihydro-9-O-(2-phenylethyl)desmycosin or salts thereof.

* * * * *